United States Patent
Chung et al.

(10) Patent No.: US 10,457,741 B2
(45) Date of Patent: Oct. 29, 2019

(54) CHICKEN ANTIBODY TRANSFORMED INTO CYSTEINE AND SITE-SPECIFIC CONJUGATION USING SAME

(71) Applicant: Seoul National University R&DB Foundation, Seoul (KR)

(72) Inventors: Junho Chung, Seongnam (KR); Aerin Yoon, Seoul (KR); Jung Won Shin, Seongnam (KR); Jungwon Han, Seoul (KR)

(73) Assignee: SEOUL NATIONAL UNIVERSITY R&DB FOUNDATION, Seoul (KR)

(*) Notice: Subject to any disclaimer, the term of this patent is extended or adjusted under 35 U.S.C. 154(b) by 166 days.

(21) Appl. No.: 14/901,245

(22) PCT Filed: Jul. 3, 2014

(86) PCT No.: PCT/KR2014/005969
§ 371 (c)(1),
(2) Date: Dec. 28, 2015

(87) PCT Pub. No.: WO2015/002486
PCT Pub. Date: Jan. 8, 2015

(65) Prior Publication Data
US 2016/0215060 A1 Jul. 28, 2016

Related U.S. Application Data

(60) Provisional application No. 61/842,482, filed on Jul. 3, 2013.

(51) Int. Cl.
*C07K 16/30* (2006.01)
*C07K 16/00* (2006.01)

(52) U.S. Cl.
CPC .......... *C07K 16/3069* (2013.01); *C07K 16/00* (2013.01); *C07K 2317/10* (2013.01); *C07K 2317/23* (2013.01); *C07K 2317/567* (2013.01); *C07K 2317/622* (2013.01)

(58) Field of Classification Search
CPC ............... C07K 16/3069; C07K 16/00; C07K 2317/622; C07K 2317/567; C07K 2317/10; C07K 2317/23; A61K 47/68; A61K 47/6803; A61K 47/6817; A61K 47/6883; A61K 47/69; A61K 47/665
See application file for complete search history.

(56) References Cited

U.S. PATENT DOCUMENTS

| 4,275,149 A | 6/1981 | Litman | |
| 7,521,541 B2* | 4/2009 | Eigenbrot | C07K 16/00 424/133.1 |
| 7,723,485 B2 | 5/2010 | Junutula | |
| 2005/0037420 A1* | 2/2005 | Zhang | C07K 16/00 435/7.1 |
| 2008/0050310 A1 | 2/2008 | Ebens | |
| 2008/0247951 A1 | 10/2008 | Koch | |
| 2008/0311134 A1 | 12/2008 | Junutula | |
| 2009/0028856 A1 | 1/2009 | Chen | |
| 2009/0068202 A1 | 3/2009 | Chen | |
| 2009/0117100 A1 | 5/2009 | Mao | |
| 2011/0301334 A1 | 12/2011 | Bhakta | |

FOREIGN PATENT DOCUMENTS

| EP | 2233156 | 5/2013 |
| KR | 10-2010-0107501 | 10/2010 |
| WO | 2013/068874 | 5/2013 |
| WO | 2013/093809 | 6/2013 |

OTHER PUBLICATIONS

Rudikoff et al., Proc Natl Acad Sci USA 1982 vol. 79 pp. 1979-1983.*
Wu et al., Journal of Molecular Biology, 1999, vol. 294, pp. 151-162.*
Shen et al., Nature Biotechnology 30(2): 184-189, Feb. 2012.*
Lloyd et al., Protein Engineering, Design & Selection 22:159-168 (Year: 2009).*
Edwards et al., J Mol Biol. 334(1): 103-118 (Year: 2003).*
Rudikoff et al., PNAS 79: 1979-1983 (Year: 1982).*
Vajdos et al., J. Mol. Biol. 320(2):415-28 (Year: 2002).*
Wu et al., J Mol Biol 294: 151-162 (Year: 1999).*
Junutula et al., "Rapid identification of reactive cysteine residues for site-specific labeling of antibody-Fabs", Journal of Immunological Methods, vol. 332, No. 1-2, pp. 41-52, Jan. 14, 2008.
European Patent Office, Extended European Search Report of EP 14819598.5, dated Jan. 23, 2017.
Wu L. et al., "Fundamental Characteristics of the Immunoglobulin VH Repertoire of Chickens in Comparison with Those of Humans, Mice, and Camelids", J. Immunol., 188, p. 322-333, Jan. 1, 2012.
Voynov V. et al., "Design and Application of Antibody Cysteine Variants", Bioconjugate Chem., 21, p. 385-392, Jan. 21, 2010.

(Continued)

*Primary Examiner* — Phuong Huynh
(74) *Attorney, Agent, or Firm* — Lex IP Meister, PLLC

(57) ABSTRACT

A framework fragment derived from a chicken antibody, in which an amino acid at a particular position is replaced by cysteine, a heavy chain variable region or a light chain variable region including the framework fragment, or an antibody including the heavy chain variable region or the light chain variable region does not induce or prevents formation of disulfide bonds between antibody molecules while maintaining activity and reactivity of the antibody. The antibody introduced with cysteine or an antigen-binding fragment thereof easily binds with a conjugation compound such as a chemotherapeutic drug, an enzyme, an aptamer, a toxin, an affinity ligand, or a detection label, thereby being applied to various fields for diagnosis or treatment of diseases.

3 Claims, 22 Drawing Sheets

Specification includes a Sequence Listing.

(56) References Cited

OTHER PUBLICATIONS

Chen X. et al., "Charge-based analysis of antibodies with engineered cysteines", mAbs, 1:6, p. 563-571, Nov. 1, 2009.

Shen, et al., "Conjugation site modulates the in vivo stability and therapeutic activity of antibody-drug conjugates", Nature Biotechnology, vol. 30, No. 2, pp. 184-189, Jan. 22, 2012.

Goldenberg D. M. et al., "Use of RadioLabeled Antibodies to Carcinoembryonic Antigen for the Detection and Localization of Diverse Cancers by External Photoscanning", N. Engl. J. Med., Jun. 22, 1978, 298:1384-1386.

Stimmel J.B. et al., "Site-specific Conjugation on Serine 3 Cysteine Variant Monoclonal Antibodies", J. Biol. Chem. Sep. 29, 2000, 273: 30445-30450.

Zhang W. et al., "Complete disulfide bond assignment of a recombinant immunoglobulin G4 monoclonal antibody", Anal. Biochem., Dec. 1, 2002, 311:1-9.

Olafsen T. et al., "Characterization of engineered anti-p185HER-2 (scFv-CH3)2 antibody fragments (minibodies) for tumor targeting", Protein Eng. Design & Sel., Jun. 8, 2004, 17:315-323.

Chacko A.M et al., "Targeted delivery of antibody-based therapeutic and imaging agents to CNS tumors: crossing the blood-brain barrier divide", Expert Opin. Drug Deliv., Jun. 11, 2013, 10: 907-26.

Andris-Widhopf J. et al., "Methods for the generation of chicken monoclonal antibody fragments by phage display", J Immunol. Methods, Aug. 28, 2000, 242: 159-181.

Chung J. et al., "Integrin AIIbB3-specific synthetic human monoclonal antibodies and HCDR3 peptides that potently inhibit platelet aggregation1", FASEB J., Feb. 2004, 18: 361-383.

Shih H.H. et al., "An Ultra-specific Avian Antibody to Phosphorylated Tau Protein Reveals a Unique Mechanism for Phosphoepitope Recognition", J Biol. Chem., Dec. 28, 2012, 287:44425-44434; PDB ID: 4GLR.

Junutula et al., "Site-specific conjugation of a cytotoxic drug to an antibody improves the therapeutic index", Jul. 20, 2008, nature biotechnology, 925-932.

Shen B.Q. et al., "Conjugation site modulates the in vivo stability and therapeutic activity of antibody-drug conjugates", Nat. Biotechnol., Jan. 22, 2012, 30: 184-189.

Rainsbury R. M. et al., "Location of Metastatic Breast Carcinoma by a Monoclonal Antibody Chelate Labelled With Indium-111", The Lancet, Oct. 22, 1983, 2:934-938.

Yamada H.et al., "Selective Modification of Aspartic Acid-10 1 in Lysozyme by Carbodiimide Reaction", Biochemistry, Aug. 1981, 20:4836-4842.

Wang Li-meng et al., "Construction and selection of camelized human sdAbs library against TNF-alpha", Mil Med Sci, vol. 37, No. 5, May, 2013.

Li Boohua et al., "Preparation and characterization of an anti-human CD3 humanized antibody", Ph. D. thesis, Abstract only,Second Military Medical University, Mar. 2002.

\* cited by examiner

FIG. 1a

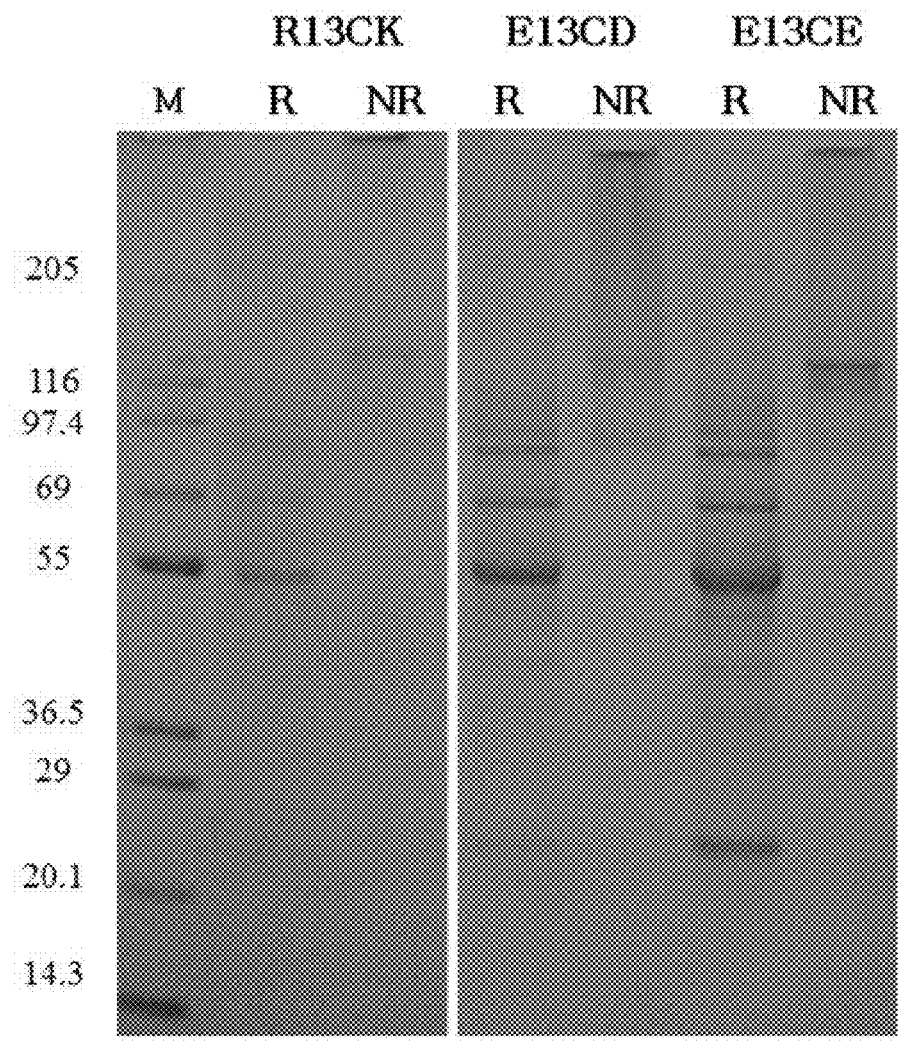

a: PEG-conjugated scFv-C$_{kappa}$ fusion protein b: scFv-C$_{kappa}$ fusion protein a: PEG-conjugated scFv-C_kappa fusion protein a: PEG-conjugated scFv-C_kappa fusion protein
b: scFv-C_kappa fusion protein a: PEG-conjugated light chain
b: PEG-conjugated heavy chain blot: anti-C-kappa HRP
a: PEG-conjugated light chain
b: light chain blot: anti-human-Fc HRP
c: PEG-conjugated heavy chain
d: heavy chain a: PEG-conjugated scFv-C$_{kappa}$ fusion protein b: scFv-C$_{kappa}$ fusion protein a: PEG-conjugated scFv-C$_{kappa}$ fusion protein a: PEG-conjugated scFv-C_kappa fusion protein
b: scFv-C_kappa fusion protein a: PEG가 접합된 중쇄: PEG-conjugated heavy chain
b: heavy chain a: PEG-conjugated heavy chain a: PEG-conjugated heavy chain
b: heavy chain

SEQUENCE LISTING

```
<160> NUMBER OF SEQ ID NOS: 88

<210> SEQ ID NO 1
<211> LENGTH: 20
<212> TYPE: PRT
<213> ORGANISM: Artificial Sequence
<220> FEATURE:
<223> OTHER INFORMATION: Framework 1 in the light chain variable region
      of wild-type chicken antibody

<400> SEQUENCE: 1

Ala Leu Thr Gln Pro Ser Ser Val Ser Ala Asn Leu Gly Gly Thr Val
1               5                   10                  15

Lys Ile Thr Cys
            20

<210> SEQ ID NO 2
<211> LENGTH: 16
<212> TYPE: PRT
<213> ORGANISM: Artificial Sequence
<220> FEATURE:
<223> OTHER INFORMATION: Framework 2 in the light chain variable region
      of wild-type chicken antibody

<400> SEQUENCE: 2

Trp Tyr Gln Gln Lys Ser Pro Gly Ser Ala Pro Val Thr Val Ile Tyr
1               5                   10                  15

<210> SEQ ID NO 3
<211> LENGTH: 32
<212> TYPE: PRT
<213> ORGANISM: Artificial Sequence
<220> FEATURE:
<223> OTHER INFORMATION: Framework 3 in the light chain variable region
      of wild-type chicken antibody

<400> SEQUENCE: 3

Asn Ile Pro Ser Arg Phe Ser Gly Ser Thr Ser Gly Ser Thr Gly Thr
1               5                   10                  15

Leu Thr Ile Thr Gly Val Gln Ala Asp Asp Ala Ala Val Tyr Tyr Cys
            20                  25                  30
```

<210> SEQ ID NO 4
<211> LENGTH: 10
<212> TYPE: PRT
<213> ORGANISM: Artificial Sequence
<220> FEATURE:
<223> OTHER INFORMATION: Framework 4 in the light chain variable region
      of wild-type chicken antibody

<400> SEQUENCE: 4

Phe Gly Ala Gly Thr Thr Leu Thr Val Leu
1               5                   10

<210> SEQ ID NO 5
<211> LENGTH: 25
<212> TYPE: PRT
<213> ORGANISM: Artificial Sequence
<220> FEATURE:
<223> OTHER INFORMATION: Framework 1 in the heavy chain variable region
      of wild-type chicken antibody

<400> SEQUENCE: 5

Ala Val Thr Leu Asp Glu Ser Gly Gly Gly Leu Gln Thr Pro Gly Gly
1               5                   10                  15

Ala Leu Ser Leu Val Cys Lys Ala Ser
            20                  25

<210> SEQ ID NO 6
<211> LENGTH: 14
<212> TYPE: PRT
<213> ORGANISM: Artificial Sequence
<220> FEATURE:
<223> OTHER INFORMATION: Framework 2 in the heavy chain variable region
      of wild-type chicken antibody

<400> SEQUENCE: 6

Trp Val Arg Gln Ala Pro Gly Lys Gly Leu Glu Trp Val Ala
1               5                   10

<210> SEQ ID NO 7
<211> LENGTH: 32
<212> TYPE: PRT
<213> ORGANISM: Artificial Sequence
<220> FEATURE:
<223> OTHER INFORMATION: Framework 3 in the heavy chain variable region
      of wild-type chicken antibody

<400> SEQUENCE: 7

Arg Ala Thr Ile Ser Arg Asp Asn Gly Gln Ser Thr Val Arg Leu Gln
1               5                   10                  15

Leu Asn Asn Leu Arg Ala Glu Asp Thr Gly Thr Tyr Phe Cys Ala Lys
            20                  25                  30

<210> SEQ ID NO 8
<211> LENGTH: 11
<212> TYPE: PRT
<213> ORGANISM: Artificial Sequence
<220> FEATURE:
<223> OTHER INFORMATION: Framework 4 in the heavy chain variable region
      of wild-type chicken antibody

<400> SEQUENCE: 8

Trp Gly His Gly Thr Glu Val Ile Val Ser Ser
1               5                   10

<210> SEQ ID NO 9

```
<211> LENGTH: 5
<212> TYPE: PRT
<213> ORGANISM: Artificial Sequence
<220> FEATURE:
<223> OTHER INFORMATION: L2CR sequence of five amino acids including
      substituted amino acid(s) in the engineered chicken framework

<400> SEQUENCE: 9

Ala Leu Cys Arg Pro
1               5

<210> SEQ ID NO 10
<211> LENGTH: 5
<212> TYPE: PRT
<213> ORGANISM: Artificial Sequence
<220> FEATURE:
<223> OTHER INFORMATION: L2CK sequence of five amino acids including
      substituted amino acid(s) in the engineered chicken framework

<400> SEQUENCE: 10

Ala Leu Cys Lys Pro
1               5

<210> SEQ ID NO 11
<211> LENGTH: 5
<212> TYPE: PRT
<213> ORGANISM: Artificial Sequence
<220> FEATURE:
<223> OTHER INFORMATION: R2CQ sequence of five amino acids including
      substituted amino acid(s) in the engineered chicken framework

<400> SEQUENCE: 11

Ala Arg Cys Gln Pro
1               5

<210> SEQ ID NO 12
<211> LENGTH: 5
<212> TYPE: PRT
<213> ORGANISM: Artificial Sequence
<220> FEATURE:
<223> OTHER INFORMATION: R2CR sequence of five amino acids including
      substituted amino acid(s) in the engineered chicken framework

<400> SEQUENCE: 12

Ala Arg Cys Arg Pro
1               5

<210> SEQ ID NO 13
<211> LENGTH: 5
<212> TYPE: PRT
<213> ORGANISM: Artificial Sequence
<220> FEATURE:
<223> OTHER INFORMATION: R2CK sequence of five amino acids including
      substituted amino acid(s) in the engineered chicken framework

<400> SEQUENCE: 13

Ala Arg Cys Lys Pro
1               5

<210> SEQ ID NO 14
<211> LENGTH: 5
<212> TYPE: PRT
<213> ORGANISM: Artificial Sequence
<220> FEATURE:
<223> OTHER INFORMATION: K2CQ sequence of five amino acids including
      substituted amino acid(s) in the engineered chicken framework

<400> SEQUENCE: 14
```

```
Ala Lys Cys Gln Pro
1               5

<210> SEQ ID NO 15
<211> LENGTH: 5
<212> TYPE: PRT
<213> ORGANISM: Artificial Sequence
<220> FEATURE:
<223> OTHER INFORMATION: K2CR sequence of five amino acids including
      substituted amino acid(s) in the engineered chicken framework

<400> SEQUENCE: 15

Ala Lys Cys Arg Pro
1               5

<210> SEQ ID NO 16
<211> LENGTH: 5
<212> TYPE: PRT
<213> ORGANISM: Artificial Sequence
<220> FEATURE:
<223> OTHER INFORMATION: K2CK sequence of five amino acids including
      substituted amino acid(s) in the engineered chicken framework

<400> SEQUENCE: 16

Ala Lys Cys Lys Pro
1               5

<210> SEQ ID NO 17
<211> LENGTH: 5
<212> TYPE: PRT
<213> ORGANISM: Artificial Sequence
<220> FEATURE:
<223> OTHER INFORMATION: L2CD sequence of five amino acids including
      substituted amino acid(s) in the engineered chicken framework

<400> SEQUENCE: 17

Ala Leu Cys Asp Pro
1               5

<210> SEQ ID NO 18
<211> LENGTH: 5
<212> TYPE: PRT
<213> ORGANISM: Artificial Sequence
<220> FEATURE:
<223> OTHER INFORMATION: L2CE sequence of five amino acids including
      substituted amino acid(s) in the engineered chicken framework

<400> SEQUENCE: 18

Ala Leu Cys Glu Pro
1               5

<210> SEQ ID NO 19
<211> LENGTH: 5
<212> TYPE: PRT
<213> ORGANISM: Artificial Sequence
<220> FEATURE:
<223> OTHER INFORMATION: D2CQ sequence of five amino acids including
      substituted amino acid(s) in the engineered chicken framework

<400> SEQUENCE: 19

Ala Asp Cys Gln Pro
1               5

<210> SEQ ID NO 20
<211> LENGTH: 5
<212> TYPE: PRT
<213> ORGANISM: Artificial Sequence
<220> FEATURE:
```

<223> OTHER INFORMATION: D2CD sequence of five amino acids including
      substituted amino acid(s) in the engineered chicken framework

<400> SEQUENCE: 20

Ala Asp Cys Asp Pro
1               5

<210> SEQ ID NO 21
<211> LENGTH: 5
<212> TYPE: PRT
<213> ORGANISM: Artificial Sequence
<220> FEATURE:
<223> OTHER INFORMATION: D2CE sequence of five amino acids including
      substituted amino acid(s) in the engineered chicken framework

<400> SEQUENCE: 21

Ala Asp Cys Glu Pro
1               5

<210> SEQ ID NO 22
<211> LENGTH: 5
<212> TYPE: PRT
<213> ORGANISM: Artificial Sequence
<220> FEATURE:
<223> OTHER INFORMATION: E2CQ sequence of five amino acids including
      substituted amino acid(s) in the engineered chicken framework

<400> SEQUENCE: 22

Ala Glu Cys Gln Pro
1               5

<210> SEQ ID NO 23
<211> LENGTH: 5
<212> TYPE: PRT
<213> ORGANISM: Artificial Sequence
<220> FEATURE:
<223> OTHER INFORMATION: E2CD sequence of five amino acids including
      substituted amino acid(s) in the engineered chicken framework

<400> SEQUENCE: 23

Ala Glu Cys Asp Pro
1               5

<210> SEQ ID NO 24
<211> LENGTH: 5
<212> TYPE: PRT
<213> ORGANISM: Artificial Sequence
<220> FEATURE:
<223> OTHER INFORMATION: E2CE sequence of five amino acids including
      substituted amino acid(s) in the engineered chicken framework

<400> SEQUENCE: 24

Ala Glu Cys Glu Pro
1               5

<210> SEQ ID NO 25
<211> LENGTH: 5
<212> TYPE: PRT
<213> ORGANISM: Artificial Sequence
<220> FEATURE:
<223> OTHER INFORMATION: T3CR sequence of five amino acids including
      substituted amino acid(s) in the engineered chicken framework

<400> SEQUENCE: 25

Leu Thr Cys Arg Ser
1               5

```
<210> SEQ ID NO 26
<211> LENGTH: 5
<212> TYPE: PRT
<213> ORGANISM: Artificial Sequence
<220> FEATURE:
<223> OTHER INFORMATION: T3CK sequence of five amino acids including
      substituted amino acid(s) in the engineered chicken framework

<400> SEQUENCE: 26

Leu Thr Cys Lys Ser
1               5

<210> SEQ ID NO 27
<211> LENGTH: 5
<212> TYPE: PRT
<213> ORGANISM: Artificial Sequence
<220> FEATURE:
<223> OTHER INFORMATION: R3CP sequence of five amino acids including
      substituted amino acid(s) in the engineered chicken framework

<400> SEQUENCE: 27

Leu Arg Cys Pro Ser
1               5

<210> SEQ ID NO 28
<211> LENGTH: 5
<212> TYPE: PRT
<213> ORGANISM: Artificial Sequence
<220> FEATURE:
<223> OTHER INFORMATION: R3CR sequence of five amino acids including
      substituted amino acid(s) in the engineered chicken framework

<400> SEQUENCE: 28

Leu Arg Cys Arg Ser
1               5

<210> SEQ ID NO 29
<211> LENGTH: 5
<212> TYPE: PRT
<213> ORGANISM: Artificial Sequence
<220> FEATURE:
<223> OTHER INFORMATION: R3CK sequence of five amino acids including
      substituted amino acid(s) in the engineered chicken framework

<400> SEQUENCE: 29

Leu Arg Cys Lys Ser
1               5

<210> SEQ ID NO 30
<211> LENGTH: 5
<212> TYPE: PRT
<213> ORGANISM: Artificial Sequence
<220> FEATURE:
<223> OTHER INFORMATION: K3CP sequence of five amino acids including
      substituted amino acid(s) in the engineered chicken framework

<400> SEQUENCE: 30

Leu Lys Cys Pro Ser
1               5

<210> SEQ ID NO 31
<211> LENGTH: 5
<212> TYPE: PRT
<213> ORGANISM: Artificial Sequence
<220> FEATURE:
<223> OTHER INFORMATION: K3CR sequence of five amino acids including
      substituted amino acid(s) in the engineered chicken framework

<400> SEQUENCE: 31
```

```
Leu Lys Cys Arg Ser
1               5

<210> SEQ ID NO 32
<211> LENGTH: 5
<212> TYPE: PRT
<213> ORGANISM: Artificial Sequence
<220> FEATURE:
<223> OTHER INFORMATION: K3CK sequence of five amino acids including
      substituted amino acid(s) in the engineered chicken framework

<400> SEQUENCE: 32

Leu Lys Cys Lys Ser
1               5

<210> SEQ ID NO 33
<211> LENGTH: 5
<212> TYPE: PRT
<213> ORGANISM: Artificial Sequence
<220> FEATURE:
<223> OTHER INFORMATION: T3CD sequence of five amino acids including
      substituted amino acid(s) in the engineered chicken framework

<400> SEQUENCE: 33

Leu Thr Cys Asp Ser
1               5

<210> SEQ ID NO 34
<211> LENGTH: 5
<212> TYPE: PRT
<213> ORGANISM: Artificial Sequence
<220> FEATURE:
<223> OTHER INFORMATION: T3CE sequence of five amino acids including
      substituted amino acid(s) in the engineered chicken framework

<400> SEQUENCE: 34

Leu Thr Cys Glu Ser
1               5

<210> SEQ ID NO 35
<211> LENGTH: 5
<212> TYPE: PRT
<213> ORGANISM: Artificial Sequence
<220> FEATURE:
<223> OTHER INFORMATION: D3CP sequence of five amino acids including
      substituted amino acid(s) in the engineered chicken framework

<400> SEQUENCE: 35

Leu Asp Cys Pro Ser
1               5

<210> SEQ ID NO 36
<211> LENGTH: 5
<212> TYPE: PRT
<213> ORGANISM: Artificial Sequence
<220> FEATURE:
<223> OTHER INFORMATION: D3CD sequence of five amino acids including
      substituted amino acid(s) in the engineered chicken framework

<400> SEQUENCE: 36

Leu Asp Cys Asp Ser
1               5

<210> SEQ ID NO 37
<211> LENGTH: 5
<212> TYPE: PRT
<213> ORGANISM: Artificial Sequence
```

```
<220> FEATURE:
<223> OTHER INFORMATION: D3CE sequence of five amino acids including
      substituted amino acid(s) in the engineered chicken framework

<400> SEQUENCE: 37

Leu Asp Cys Glu Ser
1               5

<210> SEQ ID NO 38
<211> LENGTH: 5
<212> TYPE: PRT
<213> ORGANISM: Artificial Sequence
<220> FEATURE:
<223> OTHER INFORMATION: E3CP sequence of five amino acids including
      substituted amino acid(s) in the engineered chicken framework

<400> SEQUENCE: 38

Leu Glu Cys Pro Ser
1               5

<210> SEQ ID NO 39
<211> LENGTH: 5
<212> TYPE: PRT
<213> ORGANISM: Artificial Sequence
<220> FEATURE:
<223> OTHER INFORMATION: E3CD sequence of five amino acids including
      substituted amino acid(s) in the engineered chicken framework

<400> SEQUENCE: 39

Leu Glu Cys Asp Ser
1               5

<210> SEQ ID NO 40
<211> LENGTH: 5
<212> TYPE: PRT
<213> ORGANISM: Artificial Sequence
<220> FEATURE:
<223> OTHER INFORMATION: E3CE sequence of five amino acids including
      substituted amino acid(s) in the engineered chicken framework

<400> SEQUENCE: 40

Leu Glu Cys Glu Ser
1               5

<210> SEQ ID NO 41
<211> LENGTH: 5
<212> TYPE: PRT
<213> ORGANISM: Artificial Sequence
<220> FEATURE:
<223> OTHER INFORMATION: Q4CR sequence of five amino acids including
      substituted amino acid(s) in the engineered chicken framework

<400> SEQUENCE: 41

Thr Gln Cys Arg Ser
1               5

<210> SEQ ID NO 42
<211> LENGTH: 5
<212> TYPE: PRT
<213> ORGANISM: Artificial Sequence
<220> FEATURE:
<223> OTHER INFORMATION: Q4CK sequence of five amino acids including
      substituted amino acid(s) in the engineered chicken framework

<400> SEQUENCE: 42

Thr Gln Cys Lys Ser
1               5
```

<210> SEQ ID NO 43
<211> LENGTH: 5
<212> TYPE: PRT
<213> ORGANISM: Artificial Sequence
<220> FEATURE:
<223> OTHER INFORMATION: R4CS sequence of five amino acids including
      substituted amino acid(s) in the engineered chicken framework

<400> SEQUENCE: 43

Thr Arg Cys Ser Ser
1               5

<210> SEQ ID NO 44
<211> LENGTH: 5
<212> TYPE: PRT
<213> ORGANISM: Artificial Sequence
<220> FEATURE:
<223> OTHER INFORMATION: R4CR sequence of five amino acids including
      substituted amino acid(s) in the engineered chicken framework

<400> SEQUENCE: 44

Thr Arg Cys Arg Ser
1               5

<210> SEQ ID NO 45
<211> LENGTH: 5
<212> TYPE: PRT
<213> ORGANISM: Artificial Sequence
<220> FEATURE:
<223> OTHER INFORMATION: R4CK sequence of five amino acids including
      substituted amino acid(s) in the engineered chicken framework

<400> SEQUENCE: 45

Thr Arg Cys Lys Ser
1               5

<210> SEQ ID NO 46
<211> LENGTH: 5
<212> TYPE: PRT
<213> ORGANISM: Artificial Sequence
<220> FEATURE:
<223> OTHER INFORMATION: K4CS sequence of five amino acids including
      substituted amino acid(s) in the engineered chicken framework

<400> SEQUENCE: 46

Thr Lys Cys Ser Ser
1               5

<210> SEQ ID NO 47
<211> LENGTH: 5
<212> TYPE: PRT
<213> ORGANISM: Artificial Sequence
<220> FEATURE:
<223> OTHER INFORMATION: K4CR sequence of five amino acids including
      substituted amino acid(s) in the engineered chicken framework

<400> SEQUENCE: 47

Thr Lys Cys Arg Ser
1               5

<210> SEQ ID NO 48
<211> LENGTH: 5
<212> TYPE: PRT
<213> ORGANISM: Artificial Sequence
<220> FEATURE:
<223> OTHER INFORMATION: K4CK sequence of five amino acids including
      substituted amino acid(s) in the engineered chicken framework

```
<400> SEQUENCE: 48

Thr Lys Cys Lys Ser
1               5

<210> SEQ ID NO 49
<211> LENGTH: 5
<212> TYPE: PRT
<213> ORGANISM: Artificial Sequence
<220> FEATURE:
<223> OTHER INFORMATION: Q4CD sequence of five amino acids including
      substituted amino acid(s) in the engineered chicken framework

<400> SEQUENCE: 49

Thr Gln Cys Asp Ser
1               5

<210> SEQ ID NO 50
<211> LENGTH: 5
<212> TYPE: PRT
<213> ORGANISM: Artificial Sequence
<220> FEATURE:
<223> OTHER INFORMATION: Q4CE sequence of five amino acids including
      substituted amino acid(s) in the engineered chicken framework

<400> SEQUENCE: 50

Thr Gln Cys Glu Ser
1               5

<210> SEQ ID NO 51
<211> LENGTH: 5
<212> TYPE: PRT
<213> ORGANISM: Artificial Sequence
<220> FEATURE:
<223> OTHER INFORMATION: D4CS sequence of five amino acids including
      substituted amino acid(s) in the engineered chicken framework

<400> SEQUENCE: 51

Thr Asp Cys Ser Ser
1               5

<210> SEQ ID NO 52
<211> LENGTH: 5
<212> TYPE: PRT
<213> ORGANISM: Artificial Sequence
<220> FEATURE:
<223> OTHER INFORMATION: D4CD sequence of five amino acids including
      substituted amino acid(s) in the engineered chicken framework

<400> SEQUENCE: 52

Thr Asp Cys Asp Ser
1               5

<210> SEQ ID NO 53
<211> LENGTH: 5
<212> TYPE: PRT
<213> ORGANISM: Artificial Sequence
<220> FEATURE:
<223> OTHER INFORMATION: D4CE sequence of five amino acids including
      substituted amino acid(s) in the engineered chicken framework

<400> SEQUENCE: 53

Thr Asp Cys Glu Ser
1               5

<210> SEQ ID NO 54
<211> LENGTH: 5
<212> TYPE: PRT
```

<213> ORGANISM: Artificial Sequence
<220> FEATURE:
<223> OTHER INFORMATION: E4CS sequence of five amino acids including
      substituted amino acid(s) in the engineered chicken framework

<400> SEQUENCE: 54

Thr Glu Cys Ser Ser
1               5

<210> SEQ ID NO 55
<211> LENGTH: 5
<212> TYPE: PRT
<213> ORGANISM: Artificial Sequence
<220> FEATURE:
<223> OTHER INFORMATION: E4CD sequence of five amino acids including
      substituted amino acid(s) in the engineered chicken framework

<400> SEQUENCE: 55

Thr Glu Cys Asp Ser
1               5

<210> SEQ ID NO 56
<211> LENGTH: 5
<212> TYPE: PRT
<213> ORGANISM: Artificial Sequence
<220> FEATURE:
<223> OTHER INFORMATION: E4CE sequence of five amino acids including
      substituted amino acid(s) in the engineered chicken framework

<400> SEQUENCE: 56

Thr Glu Cys Glu Ser
1               5

<210> SEQ ID NO 57
<211> LENGTH: 5
<212> TYPE: PRT
<213> ORGANISM: Artificial Sequence
<220> FEATURE:
<223> OTHER INFORMATION: Q13CR sequence of five amino acids including
      substituted amino acid(s) in the engineered chicken framework

<400> SEQUENCE: 57

Leu Gln Cys Arg Gly
1               5

<210> SEQ ID NO 58
<211> LENGTH: 5
<212> TYPE: PRT
<213> ORGANISM: Artificial Sequence
<220> FEATURE:
<223> OTHER INFORMATION: Q13CK sequence of five amino acids including
      substituted amino acid(s) in the engineered chicken framework

<400> SEQUENCE: 58

Leu Gln Cys Lys Gly
1               5

<210> SEQ ID NO 59
<211> LENGTH: 5
<212> TYPE: PRT
<213> ORGANISM: Artificial Sequence
<220> FEATURE:
<223> OTHER INFORMATION: R13CP sequence of five amino acids including
      substituted amino acid(s) in the engineered chicken framework

<400> SEQUENCE: 59

Leu Arg Cys Pro Gly
1               5

```
<210> SEQ ID NO 60
<211> LENGTH: 5
<212> TYPE: PRT
<213> ORGANISM: Artificial Sequence
<220> FEATURE:
<223> OTHER INFORMATION: R13CR sequence of five amino acids including
      substituted amino acid(s) in the engineered chicken framework

<400> SEQUENCE: 60

Leu Arg Cys Arg Gly
1               5

<210> SEQ ID NO 61
<211> LENGTH: 5
<212> TYPE: PRT
<213> ORGANISM: Artificial Sequence
<220> FEATURE:
<223> OTHER INFORMATION: R13CK sequence of five amino acids including
      substituted amino acid(s) in the engineered chicken framework

<400> SEQUENCE: 61

Leu Arg Cys Lys Gly
1               5

<210> SEQ ID NO 62
<211> LENGTH: 5
<212> TYPE: PRT
<213> ORGANISM: Artificial Sequence
<220> FEATURE:
<223> OTHER INFORMATION: K13CP sequence of five amino acids including
      substituted amino acid(s) in the engineered chicken framework

<400> SEQUENCE: 62

Leu Lys Cys Pro Gly
1               5

<210> SEQ ID NO 63
<211> LENGTH: 5
<212> TYPE: PRT
<213> ORGANISM: Artificial Sequence
<220> FEATURE:
<223> OTHER INFORMATION: K13CR sequence of five amino acids including
      substituted amino acid(s) in the engineered chicken framework

<400> SEQUENCE: 63

Leu Lys Cys Arg Gly
1               5

<210> SEQ ID NO 64
<211> LENGTH: 5
<212> TYPE: PRT
<213> ORGANISM: Artificial Sequence
<220> FEATURE:
<223> OTHER INFORMATION: K13CK sequence of five amino acids including
      substituted amino acid(s) in the engineered chicken framework

<400> SEQUENCE: 64

Leu Lys Cys Lys Gly
1               5

<210> SEQ ID NO 65
<211> LENGTH: 5
<212> TYPE: PRT
<213> ORGANISM: Artificial Sequence
<220> FEATURE:
<223> OTHER INFORMATION: Q13CD sequence of five amino acids including
      substituted amino acid(s) in the engineered chicken framework
```

```
<400> SEQUENCE: 65

Leu Gln Cys Asp Gly
1               5

<210> SEQ ID NO 66
<211> LENGTH: 5
<212> TYPE: PRT
<213> ORGANISM: Artificial Sequence
<220> FEATURE:
<223> OTHER INFORMATION: Q13CE sequence of five amino acids including
      substituted amino acid(s) in the engineered chicken framework

<400> SEQUENCE: 66

Leu Gln Cys Glu Gly
1               5

<210> SEQ ID NO 67
<211> LENGTH: 5
<212> TYPE: PRT
<213> ORGANISM: Artificial Sequence
<220> FEATURE:
<223> OTHER INFORMATION: D13CP sequence of five amino acids including
      substituted amino acid(s) in the engineered chicken framework

<400> SEQUENCE: 67

Leu Asp Cys Pro Gly
1               5

<210> SEQ ID NO 68
<211> LENGTH: 5
<212> TYPE: PRT
<213> ORGANISM: Artificial Sequence
<220> FEATURE:
<223> OTHER INFORMATION: D13CD sequence of five amino acids including
      substituted amino acid(s) in the engineered chicken framework

<400> SEQUENCE: 68

Leu Asp Cys Asp Gly
1               5

<210> SEQ ID NO 69
<211> LENGTH: 5
<212> TYPE: PRT
<213> ORGANISM: Artificial Sequence
<220> FEATURE:
<223> OTHER INFORMATION: D13CE sequence of five amino acids including
      substituted amino acid(s) in the engineered chicken framework

<400> SEQUENCE: 69

Leu Asp Cys Glu Gly
1               5

<210> SEQ ID NO 70
<211> LENGTH: 5
<212> TYPE: PRT
<213> ORGANISM: Artificial Sequence
<220> FEATURE:
<223> OTHER INFORMATION: E13CP sequence of five amino acids including
      substituted amino acid(s) in the engineered chicken framework

<400> SEQUENCE: 70

Leu Glu Cys Pro Gly
1               5

<210> SEQ ID NO 71
<211> LENGTH: 5
```

```
<212> TYPE: PRT
<213> ORGANISM: Artificial Sequence
<220> FEATURE:
<223> OTHER INFORMATION: E13CD sequence of five amino acids including
      substituted amino acid(s) in the engineered chicken framework

<400> SEQUENCE: 71

Leu Glu Cys Asp Gly
1               5

<210> SEQ ID NO 72
<211> LENGTH: 5
<212> TYPE: PRT
<213> ORGANISM: Artificial Sequence
<220> FEATURE:
<223> OTHER INFORMATION: E13CE sequence of five amino acids including
      substituted amino acid(s) in the engineered chicken framework

<400> SEQUENCE: 72

Leu Glu Cys Glu Gly
1               5

<210> SEQ ID NO 73
<211> LENGTH: 5
<212> TYPE: PRT
<213> ORGANISM: Artificial Sequence
<220> FEATURE:
<223> OTHER INFORMATION: G16CR sequence of five amino acids including
      substituted amino acid(s) in the engineered chicken framework

<400> SEQUENCE: 73

Pro Gly Cys Arg Leu
1               5

<210> SEQ ID NO 74
<211> LENGTH: 5
<212> TYPE: PRT
<213> ORGANISM: Artificial Sequence
<220> FEATURE:
<223> OTHER INFORMATION: G16CK sequence of five amino acids including
      substituted amino acid(s) in the engineered chicken framework

<400> SEQUENCE: 74

Pro Gly Cys Lys Leu
1               5

<210> SEQ ID NO 75
<211> LENGTH: 5
<212> TYPE: PRT
<213> ORGANISM: Artificial Sequence
<220> FEATURE:
<223> OTHER INFORMATION: R16CA sequence of five amino acids including
      substituted amino acid(s) in the engineered chicken framework

<400> SEQUENCE: 75

Pro Arg Cys Ala Leu
1               5

<210> SEQ ID NO 76
<211> LENGTH: 5
<212> TYPE: PRT
<213> ORGANISM: Artificial Sequence
<220> FEATURE:
<223> OTHER INFORMATION: R16CR sequence of five amino acids including
      substituted amino acid(s) in the engineered chicken framework

<400> SEQUENCE: 76

Pro Arg Cys Arg Leu
```

```
1               5

<210> SEQ ID NO 77
<211> LENGTH: 5
<212> TYPE: PRT
<213> ORGANISM: Artificial Sequence
<220> FEATURE:
<223> OTHER INFORMATION: R16CK sequence of five amino acids including
      substituted amino acid(s) in the engineered chicken framework

<400> SEQUENCE: 77

Pro Arg Cys Lys Leu
1               5

<210> SEQ ID NO 78
<211> LENGTH: 5
<212> TYPE: PRT
<213> ORGANISM: Artificial Sequence
<220> FEATURE:
<223> OTHER INFORMATION: K16CA sequence of five amino acids including
      substituted amino acid(s) in the engineered chicken framework

<400> SEQUENCE: 78

Pro Lys Cys Ala Leu
1               5

<210> SEQ ID NO 79
<211> LENGTH: 5
<212> TYPE: PRT
<213> ORGANISM: Artificial Sequence
<220> FEATURE:
<223> OTHER INFORMATION: K16CR sequence of five amino acids including
      substituted amino acid(s) in the engineered chicken framework

<400> SEQUENCE: 79

Pro Lys Cys Arg Leu
1               5

<210> SEQ ID NO 80
<211> LENGTH: 5
<212> TYPE: PRT
<213> ORGANISM: Artificial Sequence
<220> FEATURE:
<223> OTHER INFORMATION: K16CK sequence of five amino acids including
      substituted amino acid(s) in the engineered chicken framework

<400> SEQUENCE: 80

Pro Lys Cys Lys Leu
1               5

<210> SEQ ID NO 81
<211> LENGTH: 5
<212> TYPE: PRT
<213> ORGANISM: Artificial Sequence
<220> FEATURE:
<223> OTHER INFORMATION: G16CD sequence of five amino acids including
      substituted amino acid(s) in the engineered chicken framework

<400> SEQUENCE: 81

Pro Gly Cys Asp Leu
1               5

<210> SEQ ID NO 82
<211> LENGTH: 5
<212> TYPE: PRT
<213> ORGANISM: Artificial Sequence
<220> FEATURE:
<223> OTHER INFORMATION: G16CE sequence of five amino acids including
``` substituted amino acid(s) in the engineered chicken framework

<400> SEQUENCE: 82

Pro Gly Cys Glu Leu
1               5

<210> SEQ ID NO 83
<211> LENGTH: 5
<212> TYPE: PRT
<213> ORGANISM: Artificial Sequence
<220> FEATURE:
<223> OTHER INFORMATION: D16CA sequence of five amino acids including
      substituted amino acid(s) in the engineered chicken framework

<400> SEQUENCE: 83

Pro Asp Cys Ala Leu
1               5

<210> SEQ ID NO 84
<211> LENGTH: 5
<212> TYPE: PRT
<213> ORGANISM: Artificial Sequence
<220> FEATURE:
<223> OTHER INFORMATION: D16CD sequence of five amino acids including
      substituted amino acid(s) in the engineered chicken framework

<400> SEQUENCE: 84

Pro Asp Cys Asp Leu
1               5

<210> SEQ ID NO 85
<211> LENGTH: 5
<212> TYPE: PRT
<213> ORGANISM: Artificial Sequence
<220> FEATURE:
<223> OTHER INFORMATION: D16CE sequence of five amino acids including
      substituted amino acid(s) in the engineered chicken framework

<400> SEQUENCE: 85

Pro Asp Cys Glu Leu
1               5

<210> SEQ ID NO 86
<211> LENGTH: 5
<212> TYPE: PRT
<213> ORGANISM: Artificial Sequence
<220> FEATURE:
<223> OTHER INFORMATION: E16CA sequence of five amino acids including
      substituted amino acid(s) in the engineered chicken framework

<400> SEQUENCE: 86

Pro Glu Cys Ala Leu
1               5

<210> SEQ ID NO 87
<211> LENGTH: 5
<212> TYPE: PRT
<213> ORGANISM: Artificial Sequence
<220> FEATURE:
<223> OTHER INFORMATION: E16CD sequence of five amino acids including
      substituted amino acid(s) in the engineered chicken framework

<400> SEQUENCE: 87

Pro Glu Cys Asp Leu
1               5

<210> SEQ ID NO 88

```
<211> LENGTH: 5
<212> TYPE: PRT
<213> ORGANISM: Artificial Sequence
<220> FEATURE:
<223> OTHER INFORMATION: E16CE sequence of five amino acids including
      substituted amino acid(s) in the engineered chicken framework

<400> SEQUENCE: 88

Pro Glu Cys Glu Leu
1               5
```

CHICKEN ANTIBODY TRANSFORMED INTO CYSTEINE AND SITE-SPECIFIC CONJUGATION USING SAME

TECHNICAL FIELD

The present invention relates to engineered chicken antibodies which are modified with cysteine residues, and more particularly, to antibodies with application for treatment or diagnosis of diseases. The cysteine-modified antibodies may be conjugated with chemotherapeutic drugs, toxins, peptides, affinity ligands such as biotin, and detection labels such as radioisotopes and fluorophores, and used in the diagnosis or treatment of diseases.

BACKGROUND ART

Antibodies are widely used for diagnosis and treatment. Antibodies may have improved functions or may be provided with new functions by chemical binding with drugs, enzymes, dyes, peptides, aptamers, linkers, toxins, isotopes, etc. In the chemical binding with these substances, functional groups such as OH group of a tyrosine residue, $NH_3$ group of a lysine residue, or a carboxyl group of aspartic acid or glutamic acid of antibodies are involved (literature [Goldenberg D. M. et al., J. Med. (1978) 298:1384-1386; Rainsbury R. M. et al., Lancet (1983) 2:934-938; and Yamada H. et al., Biochemistry (1981) 20:4836-4842]).

However, these functional groups are also present in the antigen-binding sites. Therefore, if the residues in the antigen-binding sites are involved in the chemical binding, affinity of antibody to antigen may be affected. Further, in the binding reaction using cysteine, reduction of disulfide bonds within a chain (polypeptide) of an antibody molecule or between the chains is a prerequisite, which may affect activity of the protein (literature [Stimmel J. B. et al., J. Biol. Chem. (2000) 273: 30445-30450]). Further, proteins may be rendered inactive or non-specific by misfolding or loss of a tertiary structure (literature [Zhang W. et al., Anal. Biochem. (2002) 311:1-9]).

Site-specific conjugation is preferred over random amino modification as it enables chemical modification of a site away from the binding site, promoting complete retention of biological activity and allowing control over the possible number of prosthetic groups added. Cysteine-engineered antibodies have been conjugated through linkers at the newly introduced cysteine thiols with thiol-reactive linker reagents and drug-linker reagents to prepare cysteine-engineered antibody drug conjugates with anti-cancer properties, for example, anti-MUC16 (US 2008/0311134), anti-CD22 (US 2008/0050310), anti-ROBO4 (US 2008/0247951), anti-TENB2 (US 2009/0117100), anti-CD79B (US 2009/0028856; US 2009/0068202) thio ADC. However, one or more antibody heavy-chain and light-chain variable region genes exist in human or other animals, and as a result, each different antibody has a different framework sequence. Accordingly, there is a problem that the cysteine introduction site should be optimized with respect to respective antibodies.

DISCLOSURE

Technical Problem

An aspect of the present invention provides a framework fragment of a chicken antibody, in which a cysteine residue is introduced into a framework region present in a heavy chain variable region or a light chain variable region, a heavy chain variable region or a light chain variable region including the framework fragment, or an antibody including the heavy chain variable region or the light chain variable region.

Another aspect of the present invention provides a conjugate including the antibody or an antigen-binding fragment thereof and a conjugation compound, the conjugate being prepared by conjugating the conjugation compound, such as a chemotherapeutic drug, an enzyme, an aptamer, a toxin, an affinity ligand, or a detection label, to the introduced cysteine residue which is present in the framework fragment of the chicken antibody, the heavy chain variable region or light chain variable region including the framework fragment, or the chicken antibody including the heavy chain variable region or light chain variable region.

Still another aspect provides use of the conjugate including the antibody or the antigen-binding fragment thereof and the conjugation compound in the diagnosis or treatment of a disease.

Technical Solution

The present inventors have selected a residue which is able to maintain antibody activity and affinity although replaced by cysteine, from various amino acid residues present in framework regions in heavy chain variable region and light chain variable region of a chicken antibody, and also provided a framework fragment in a heavy chain variable region and light chain variable region of a chicken antibody, in which a particular amino acid of the framework fragment is modified with cysteine, a heavy chain variable region or light chain variable region including the framework, and an antibody including the heavy chain variable region or light chain variable region, or an antigen-binding fragment thereof.

Preferably, the cysteine-introduced site does not induce formation of disulfide bonds between antibody molecules so that no dimers are formed or a small amount of dimers is formed. Therefore, reactivity of cysteine is maintained. The antibody introduced with the cysteine or the antigen-binding fragment thereof easily binds with a conjugation compound such as a chemotherapeutic drug, an enzyme, an aptamer, a toxin, an affinity ligand, or a detection label, thereby being applied to various fields for diagnosis or treatment of diseases.

Further, the cysteine-modified framework according to the present invention, the heavy chain variable region or light chain variable region including the framework, and the antibody including the heavy chain variable region or light chain variable region or the antigen-binding fragment thereof are derived from a chicken antibody, and the chicken antibody possess one heavy chain variable region gene and one light chain variable region, unlike antibodies of humans or other animals. For this reason, all antibodies have the identical frameworks. Therefore, in the cysteine-modified framework according to the present invention or the antibody including the same, cysteines are located at the same positions, and thus equally applied to all antibodies produced in chickens.

Hereinafter, the present invention will be described in more detail.

An antibody according to an embodiment of the present invention is an antibody including a framework, in which one or more amino acid residues present in a framework region in a heavy chain variable region and a light chain variable region derived from a chicken antibody are replaced by cysteines.

An antibody according to another embodiment of the present invention is an antibody including the framework, in which one or more amino acid residues present in a framework region in a heavy chain variable region and a light chain variable region derived from a chicken antibody are replaced by cysteines, and one or more of the two amino acids flanking both sides of the replaced cysteine are additionally replaced by one or more charged amino acids selected from the group consisting of aspartic acid, glutamic acid, arginine, and lysine.

In the present invention, preparation of the modified antibody including the framework having the replaced cysteine is performed by using a chicken antibody possessing one heavy chain variable region gene and one light chain variable region gene, and thus the cysteine-modified antibody may be rapidly prepared without respective optimization of the introduction site of cysteine residue, unlike antibodies of humans or other animals having a plurality of heavy chain and light chain variable region genes.

In the present invention, the antibody (Cys), in which one or more amino acid residues present in the framework region in the heavy chain variable region and the light chain variable region derived from the chicken antibody are replaced by cysteine, is advantageous in that two or more amino acids as well as one amino acid are replaced by cysteines, and therefore, two conjugation compounds are conjugated thereto, or two or more different conjugation compounds are conjugated thereto to prepare a conjugate having various functions.

Further, the modified antibody according to the present invention is also advantageous in that in addition to the cysteine replacement, at least one amino acid of the two amino acids flanking both sides of the replaced cysteine is replaced by one or more charged amino acids selected from the group consisting of aspartic acid, glutamic acid, arginine, and lysine, thereby effectively inducing a covalent bond with a substance having an opposite charge, and inhibiting formation of disulfide bonds between the cysteine-modified antibodies having the same local charges to prevent antibody aggregation, and replacement of the amino acid with negatively charged aspartic acid or glutamic acid inhibits the breakage of maleimide bonds (literature [Shen B. Q. et al., Nat. Biotechnol. (2012) 30: 184-189]).

In the present invention, the amino acid at position replaceable with cysteine is an amino acid other than cysteine. Any amino acid located within the framework may be replaced, as long as it is able to maintain antibody activity and affinity even though replaced by cysteine.

The amino acids to be replaced, satisfying the above conditions, are located within the framework which is present in the light chain variable region of a chicken antibody, including framework 1 of SEQ ID NO: 1, framework 2 of SEQ ID NO: 2, framework 3 of SEQ ID NO: 3, and framework 4 of SEQ ID NO: 4, and structures of these frameworks are shown in detail in FIG. 1a.

In an embodiment of the present invention, the modified antibody may be an antibody including only a modified framework of the light chain variable region, only a modified framework of the heavy chain variable region, or both of the modified framework of the light chain variable region and the modified framework of the heavy chain variable region.

In the framework present in the light chain variable region of the chicken antibody, the amino acid to be replaced by cysteine is located at one or more positions selected from the group consisting of positions 3, 4, 5, 12, and 16 in the amino acid sequence of SEQ ID NO: 1 by sequential numbering (corresponding to positions 5, 6, 7, 14, and 18 by Kabat numbering), positions 31 and 40 in the amino acid sequence of SEQ ID NO: 2 by sequential numbering (corresponding to positions 37 and 45 by Kabat numbering), positions 52, 53, 56, 58, 59, 60, 61, 64, 65, 71, 78, and 82 in the amino acid sequence of SEQ ID NO: 3 by sequential numbering (corresponding to positions 57, 58, 61, 63, 64, 65, 66, 69, 70, 76, 83, and 87 by Kabat numbering), and positions 98 and 102 in the amino acid sequence of SEQ ID NO: 4 by sequential numbering (corresponding to positions 102 and 106 by Kabat numbering).

In the framework present in the light chain variable region, the position of the amino acid replaceable by cysteine is shown in Table 1a.

TABLE 1a

| Light chain framework | | | | |
|---|---|---|---|---|
| Light chain | Cys mutant | Sequence numbering | Kabat numbering | Wild type amino acid |
| Framework 1 | LF1-2 | L3 | L5 | T |
| | LF1-3 | L4 | L6 | Q |
| | LF1-4 | L5 | L7 | P |
| | LF1-11 | L12 | L14 | N |
| | LF1-15 | L16 | L18 | T |
| Framework 2 | LF2-3 | L31 | L37 | Q |
| | LF2-12 | L40 | L45 | V |
| Framework 3 | LF3-1 | L52 | L57 | N |
| | LF3-2 | L53 | L58 | I |
| | LF3-5 | L56 | L61 | R |
| | LF3-7 | L58 | L63 | S |
| | LF3-8 | L59 | L64 | G |
| | LF3-9 | L60 | L65 | S |
| | LF3-10 | L61 | L66 | T |
| | LF3-13 | L64 | L69 | S |
| | LF3-14 | L65 | L70 | T |
| | LF3-20 | L71 | L76 | T |
| | LF3-27 | L78 | L83 | A |
| | LF3-31 | L82 | L87 | Y |
| Framework 4 | LF4-5 | L98 | L102 | T |
| | LF4-9 | L102 | L106 | V |

The amino acids to be replaced, satisfying the above conditions, are located within the framework which is present in the heavy chain variable region of a chicken antibody, including framework 1 of SEQ ID NO: 5, framework 2 of SEQ ID NO: 6, framework 3 of SEQ ID NO: 7, and framework 4 of SEQ ID NO: 8, and structures of these frameworks are shown in detail in FIG. 1a.

In the framework present in the heavy chain variable region of the chicken antibody, the amino acid to be replaced by cysteine is located at one or more positions selected from the group consisting of positions 1, 3, 5, 6, 7, 11, 12, 13, 16, 18, 19, 24, and 25 in the amino acid sequence of SEQ ID NO: 5 by sequential numbering (corresponding to positions 1, 3, 5, 6, 7, 11, 12, 13, 16, 18, 19, 24, and 25 by Kabat numbering), positions 42 and 48 in the amino acid sequence of SEQ ID NO: 6 by sequential numbering (corresponding to positions 42 and 48 by Kabat numbering), positions 70, 73, 75, 76, 78, 87, 88, 89, 91, and 93 in the amino acid sequence of SEQ ID NO: 7 by sequential numbering (corresponding to positions 69, 72, 74, 75, 77, 83, 84, 85, 87, and 89 by Kabat numbering), and positions 123 and 126 in the amino acid sequence of SEQ ID NO: 8 by sequential numbering (corresponding to positions 110 and 113 by Kabat numbering).

In the framework present in the heavy chain variable region, the position of the amino acid replaceable by cysteine is shown in Table 1b.

TABLE 1b

Heavy chain framework

| Light chain | Cys mutant | Sequence numbering | Kabat numbering | Wild type amino acid |
|---|---|---|---|---|
| Framework 1 | HF1-1 | H1 | H1 | A |
| | HF1-3 | H3 | H3 | T |
| | HF1-5 | H5 | H5 | D |
| | HF1-6 | H6 | H6 | E |
| | HF1-7 | H7 | H7 | S |
| | HF1-11 | H11 | H11 | L |
| | HF1-12 | H12 | H12 | Q |
| | HF1-13 | H13 | H13 | T |
| | HF1-16 | H16 | H16 | G |
| | HF1-18 | H18 | H18 | L |
| | HF1-19 | H19 | H19 | S |
| | HF1-24 | H24 | H24 | A |
| | HF1-25 | H25 | H25 | S |
| Framework 2 | HF2-7 | H42 | H42 | G |
| | HF2-13 | H48 | H48 | V |
| Framework 3 | HF3-4 | H70 | H69 | I |
| | HF3-7 | H73 | H72 | D |
| | HF3-9 | H75 | H74 | G |
| | HF3-10 | H76 | H75 | Q |
| | HF3-12 | H78 | H77 | T |
| | HF3-21 | H87 | H83 | R |
| | HF3-22 | H88 | H84 | A |
| | HF3-23 | H89 | H85 | E |
| | HF3-25 | H91 | H87 | T |
| | HF3-27 | H93 | H89 | T |
| Framework 4 | HF4-8 | H123 | H110 | I |
| | HF4-11 | H126 | H113 | S |

Further, in the light chain variable region, the amino acid to be replaced by cysteine may be preferably located at one or more positions selected from the group consisting of positions 3, 4 and 5 in the amino acid sequence of SEQ ID NO: 1 by sequential numbering (corresponding to positions 5, 6, and 7 by Kabat numbering). In the heavy chain variable region, the amino acid to be replaced by cysteine may be preferably located at one or more positions selected from the group consisting of positions 13 and 16 in the amino acid sequence of SEQ ID NO: 5 by sequential numbering (corresponding to positions 13 and 16 by Kabat numbering).

In an embodiment of the present invention, at least one of the two amino acids flanking both sides of the replaced cysteine may be replaced by one or more charged amino acids selected from the group consisting of aspartic acid, glutamic acid, arginine, and lysine, in addition to replacement of cysteine at the preferred amino acid position. With respect to the modified antibody, for example, when the amino acid to be replaced by cysteine in the light chain variable region is preferably located at one or more positions selected from the group consisting of positions 3, 4 and 5 in the amino acid sequence of SEQ ID NO: 1 by sequential numbering, or the amino acid to be replaced by cysteine in the heavy chain variable region is preferably located at one or more positions selected from the group consisting of positions 13 and 16 in the amino acid sequence of SEQ ID NO: 5 by sequential numbering, the framework in which the amino acids flanking both sides of the replaced cysteine are replaced by charged amino acids may include modified sequences of Tables 3a and 3b.

TABLE 3a

| Mutant name | Sequence Kabat numbering (L3-L4-L5-L6-L7) | SEQ ID NO | Mutant name | Sequence Kabat numbering (L4-L5-L6-L7-L8) | SEQ ID NO | Mutant name | Sequence Kabat numbering (L5-L6-L7-L8-L9) | SEQ ID NO |
|---|---|---|---|---|---|---|---|---|
| L2CR | ALCRP | 9 | T3CR | LTCRS | 25 | Q4CR | TQCRS | 41 |
| L2CK | ALCKP | 10 | T3CK | LTCKS | 26 | Q4CK | TQCKS | 42 |
| R2CQ | ARCQP | 11 | R3CP | LRCPS | 27 | R4CS | TRCSS | 43 |
| R2CR | ARCRP | 12 | R3CR | LRCRS | 28 | R4CR | TRCRS | 44 |
| R2CK | ARCKP | 13 | R3CK | LRCKS | 29 | R4CK | TRCKS | 45 |
| K2CQ | AKCQP | 14 | K3CP | LKCPS | 30 | K4CS | TKCSS | 46 |
| K2CR | AKCRP | 15 | K3CR | LKCRS | 31 | K4CR | TKCRS | 47 |
| K2CK | AKCKP | 16 | K3CK | LKCKS | 32 | K4CK | TKCKS | 48 |
| L2CD | ALCDP | 17 | T3CD | LTCDS | 33 | Q4CD | TQCDS | 49 |
| L2CE | ALCEP | 18 | T3CE | LTCES | 34 | Q4CE | TQCES | 50 |
| D2CQ | ADCQP | 19 | D3CP | LDCPS | 35 | D4CS | TDCSS | 51 |
| D2CD | ADCDP | 20 | D3CD | LDCDS | 36 | D4CD | TDCDS | 52 |
| D2CE | ADCEP | 21 | D3CE | LDCES | 37 | D4CE | TDCES | 53 |
| E2CQ | AECQP | 22 | E3CP | LECPS | 38 | E4CS | TECSS | 54 |
| E2CD | AECDP | 23 | E3CD | LECDS | 39 | E4CD | TECDS | 55 |
| E2CE | AECEP | 24 | E3CE | LECES | 40 | E4CE | TECES | 56 |

TABLE 3b

| Mutant name | Sequence Kabat numbering (H11-H12-H13-H14-H15) | SEQ ID NO | Mutant name | Sequence Kabat numbering (H14-H15-H16-H17-H18) | SEQ ID NO |
|---|---|---|---|---|---|
| Q13CR | LQCRG | 57 | G16CR | PGCRL | 73 |
| Q13CK | LQCKG | 58 | G16CK | PGCKL | 74 |
| R13CP | LRCPG | 59 | R16CA | PRCAL | 75 |
| R13CR | LRCRG | 60 | R16CR | PRCRL | 76 |
| R13CK | LRCKG | 61 | R16CK | PRCKL | 77 |
| K13CP | LKCPG | 62 | K16CA | PKCAL | 78 |
| K13CR | LKCRG | 63 | K16CR | PKCRL | 79 |
| K13CK | LKCKG | 64 | K16CK | PKCKL | 80 |
| Q13CD | LQCDG | 65 | G16CD | PGCDL | 81 |
| Q13CE | LQCEG | 66 | G16CE | PGCEL | 82 |
| D13CP | LDCPG | 67 | D16CA | PDCAL | 83 |
| D13CD | LDCDG | 68 | D16CD | PDCDL | 84 |
| D13CE | LDCEG | 69 | D16CE | PDCEL | 85 |
| E13CP | LECPG | 70 | E16CA | PECAL | 86 |
| E13CD | LECDG | 71 | E16CD | PECDL | 87 |
| E13CE | LECEG | 72 | E16CE | PECEL | 88 |

Therefore, the modified antibody including replacement of adjacent amino acids as well as replacement of cysteine may be an antibody including a modified light chain variable region having one or more selected from the group consisting of amino acid sequences of SEQ ID NO: 57 to SEQ ID NO: 88, a modified heavy chain variable region having one or more selected from the group consisting of amino acid sequences of SEQ ID NO: 57 to SEQ ID NO: 88, or both of the modified light chain variable region and the modified heavy chain variable region.

Unless stated otherwise, the terms and phrases as used herein are intended to have the following meanings. As used herein, the term "antibody" is used in the broadest sense, and specifically, covers monoclonal antibodies, polyclonal antibodies, dimers, multimers, multispecific antibodies (e.g., bispecific antibodies), and antibody fragments exhibiting the desired biological activity. Antibodies may be murine, human, humanized, chimeric antibodies, or derived from other species. An antibody includes a full-length immunoglobulin molecule or an immunologically active portion of a full-length immunoglobulin molecule, i.e., a molecule containing an antigen binding site that immunospecifically binds a target antigen (such targets including, but not limited to, cancer cells or cells producing autoimmune antibodies associated with an autoimmune disease) or part thereof. The immunoglobulin disclosed herein may be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins may be derived from any species.

As used herein, the term "antibody fragments" includes a portion of a full length antibody, generally the antigen binding or variable region thereof. Examples of antibody fragments include Fab, Fab', F(ab')$_2$, and Fv fragments; diabodies; linear antibodies; minibodies (literature [Olafsen T. et al. Protein Eng. Design & Sel. (2004) 17:315-323]), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

In the present invention, the cysteine-substituted antibody may be prepared by a method including 1) inducing a mutation in a nucleic acid sequence encoding the cysteine-substituted antibody; 2) expressing the cysteine-substituted antibody; and 3) isolating and purifying the cysteine-substituted antibody. Further, the replacement of amino acids flanking both sides of the cysteine may be also performed in the same manner as in the replacement of cysteine.

In another specific embodiment of the present invention, provided is a conjugate including the modified antibody according to the present invention or an antigen-binding fragment thereof and a conjugation compound, the conjugate being prepared by conjugating the conjugation compound, such as a chemotherapeutic drug, an enzyme, a peptide, an aptamer, a toxin, an affinity ligand, or a detection label, to the modified antibody. According to the type of the conjugation compound, the conjugate may be variously applied to diagnosis or treatment of diseases.

In still another embodiment of the present invention, the antibody chemically binding to a peptide may further have a function of contributing to peptide affinity, such as effective penetration across the blood brain barrier via its receptor (literature [Chacko A. M et al., Expert Opin. Drug Deliv. (2013) 10: 907-26; patent: EP2 233 156 B 1]).

The conjugation compound may functions to (i) provide a detectable signal, (ii) interact with a second label to modify the detectable signal provided by the first or second label, e.g. FRET (fluorescence resonance energy transfer), (iii) stabilize interactions or increase affinity of binding, with antigen or ligand, (iv) affect mobility, e.g. electrophoretic mobility, or cell-permeability, by charge, hydrophobicity, shape, or other physical parameters, or (v) provide a capture moiety, in order to modulate ligand affinity, antibody/antigen binding, or ionic complexation.

Labeled cysteine-substituted antibodies may be useful in diagnostic assays, e.g., for detecting expression of an antigen of interest in specific cells, tissues, or serum. For diagnostic applications, the antibody will typically be labeled with a detectable moiety. Numerous labels are available which may be generally grouped into the following categories:

(a) Radioisotopes (radionuclides), such as $^3$H, $^{11}$C, $^{14}$C, $^{18}$F, $^{32}$P, $^{35}$S, $^{64}$Cu, $^{68}$Ga, $^{86}$Y, $^{89}$Zr, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. Radioisotope-labeled antibodies are useful in receptor targeted imaging experiments. The antibody may be labeled with ligand reagents that bind, chelate or otherwise complex a radioisotope metal where the reagent is reactive with the engineered cysteine thiol of the antibody.

(b) Fluorescent labels such as rare earth chelates (europium chelates), fluorescein types including FITC, 5-carboxyfluorescein, 6-carboxy fluorescein, etc.; rhodamine types including TAMRA, etc.; dansyl; Lissamine; cyanines; phycoerythrins; Texas Red; and analogs thereof. Fluorescent dyes and fluorescent label reagents include those which are commercially available from Invitrogen/Molecular Probes (Eugene, Oreg., USA) and Pierce Biotechnology, Inc. (Rockford, Ill., USA).

(c) Various enzyme-substrate labels are available or disclosed in literatures (U.S. Pat. No. 4,275,149). The enzyme generally catalyzes a chemical alteration of a chromogenic substrate that may be measured using various techniques. For example, the enzyme may catalyze a color change in a substrate, which may be measured spectrophotometrically. Alternatively, the enzyme may alter the fluorescence or chemiluminescence of the substrate. Techniques for quantifying a change in fluorescence are described above. Examples of enzymatic labels include luciferase, urease, peroxidase such as horseradish peroxidase (HRP), alkaline phosphatase (AP), β-galactosidase, glucoamylase, lysozyme, saccharide oxidase, etc. Techniques for conjugating enzymes to antibodies may be performed by a general method.

In still another embodiment, the cysteine-substituted antibody may be labeled through the cysteine thiol with radionuclides, fluorescent dyes, bioluminescence-triggering substrate moieties, chemiluminescence-triggering substrate moieties, enzymes, and other detection labels for imaging experiments with diagnostic, pharmacodynamic, and therapeutic applications. Generally, the labeled cysteine engineered antibody, i.e. "biomarker" or "probe", is administered by injection, perfusion, or oral ingestion to a living organism, e.g. human, rodent, or other small animal, a perfused organ, or tissue sample. The distribution of the probe is detected over a time course and represented by an image.

Effect of the Invention

A framework fragment of a chicken antibody according to the present invention, a heavy chain variable region or a light chain variable region including the framework fragment, or an antibody including the heavy chain variable region or the light chain variable region does not induce or prevents formation of disulfide bonds between antibody molecules while maintaining activity and reactivity of the antibody. The antibody introduced with cysteine or an antigen-binding fragment thereof easily binds with a conjugation compound such as a chemotherapeutic drug, an enzyme, an aptamer, a toxin, an affinity ligand, or a detection label, thereby being applied to various fields for diagnosis or treatment of mammalian cells or related diseases.

BRIEF DESCRIPTION OF DRAWINGS

FIG. 1a shows a sequential numbering scheme (top row) in comparison with the Kabat numbering scheme (bottom row) for base sequences of wild-type and germ-line of a chicken antibody used in the present experiment;

FIG. 5b shows coomassie blue staining of cationic or anionic Cys-modified full IgG-type antibodies expressed from cell culture for conjugation;

DETAILED DESCRIPTION OF THE EMBODIMENTS

The present invention will be described in more detail with reference to specific Examples of the present invention. However, the present invention is not limited to the following Examples, and it will be apparent to those skilled in the art that various modifications and changes may be made thereto without departing from the scope and spirit of the present invention. Therefore, the appended claims should be interpreted broadly, as may be consistent with the spirit and scope of the present invention.

Figure 1A:
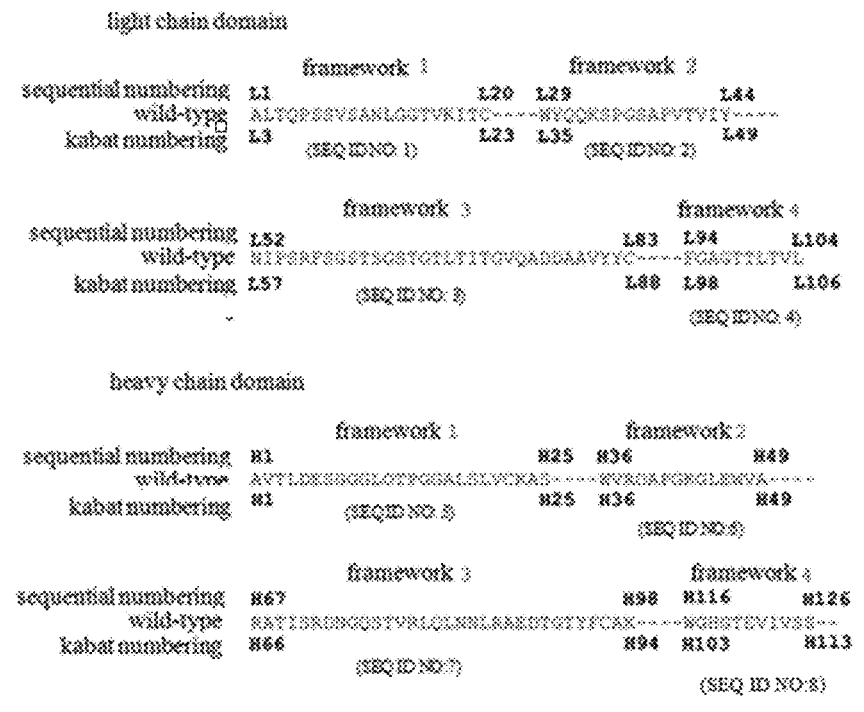
Figure 1B:
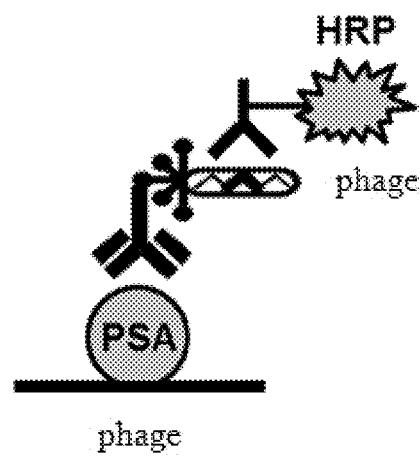
FIG. 1b shows a cartoon depiction of Cys-modified antibody phage binding to immobilized PSA with binding of anti-phage HRP antibody for absorbance detection.

Example 1: Preparation of Antibody Having One Cys Modification 1-1. Preparation of Modified Antibody Phage An antibody used in Example was a chicken antibody against PSA (prostate specific antigen), and FIG. 1a shows base sequences of frameworks of anti-PSA antibody (wild-type) and chicken germ-line ([literature [Andris-Widhopf J. et al., J Immunol. Methods (2000) 242: 159-181]). Kabat numbering system is available at http://www.bioinf.org.uk/abs/.

For preparation of Cys-modified antibody, PCR was first performed to insert NNK (N:A/C/G/T, K:G/T) into 78 light chain domain framework ($V_L$ domain framework) residues and 84 heavy chain domain framework ($V_H$ domain framework) residues in order to randomize the respective residues, in accordance with the literature [Chung J. et al., FASEB J. (2004) 18: 361-383]. Thereafter, in accordance with a method described in Barbas, C. F. (2001) Phage display: a laboratory manual. Cold Spring Harbor, N.Y.: Cold Spring Harbor Laboratory Press, the obtained scFv (single chain Fv) DNA was inserted into a phagemid vector pcomb3X, which was transformed into E. coli ER2738. Then, 92 colonies were selected according to each residue to obtain a culture supernatant containing phage-displayed scFv (single chain Fv).

Figure 1C:
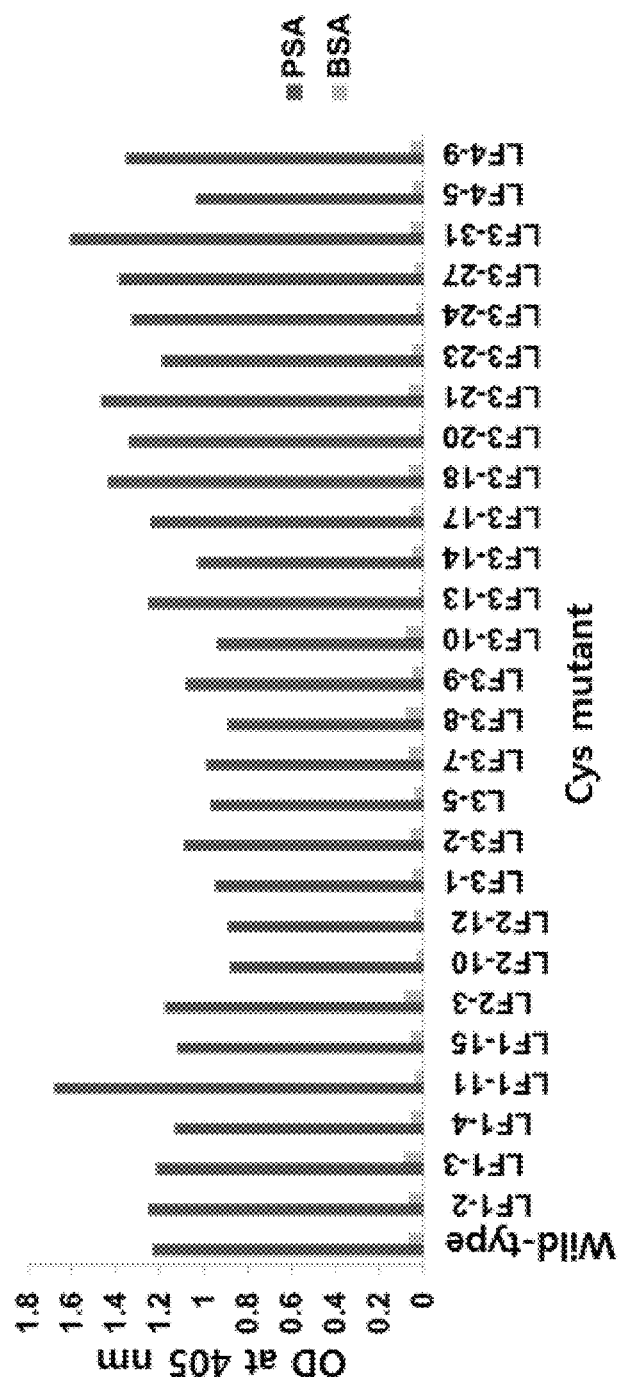
FIGS. 1c and 1d show binding measurements with detection of absorbance at 405 nm of Cys-modified antibody phages (upper: modified light chain, lower: modified heavy chain)
Figure 1D:
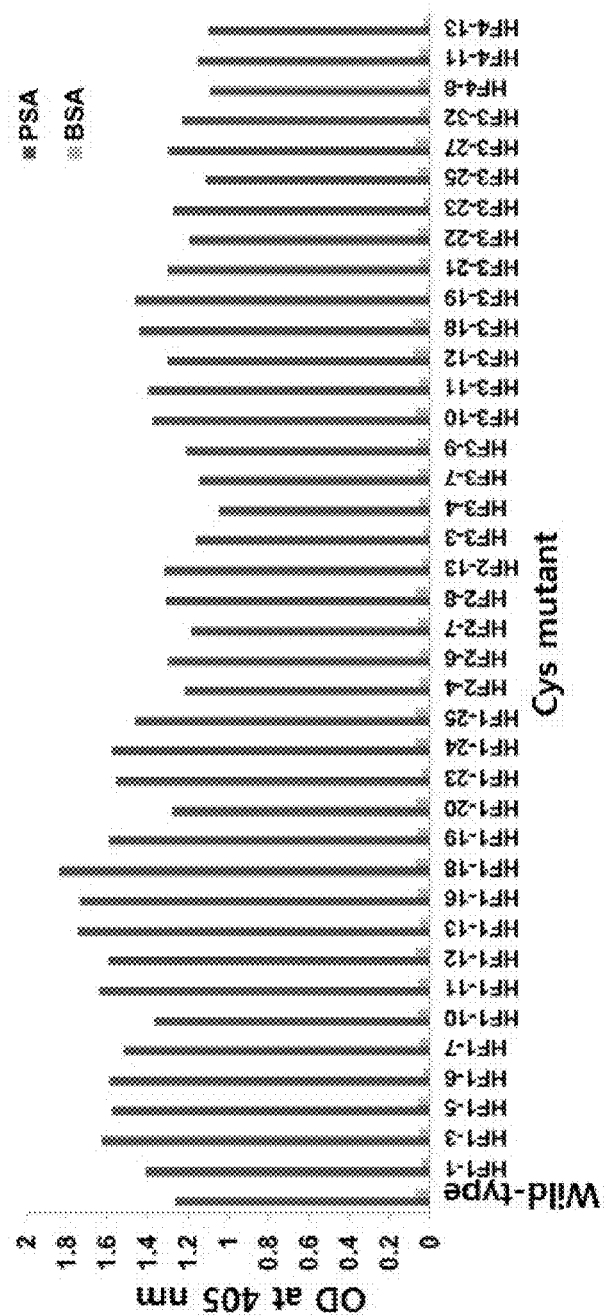

1-2. Selection of Modified Antibodies and Measurement of Their Affinity to Antigen The culture supernatant containing the phage antibodies was used to perform enzyme-linked immunosorbent assay (ELISA) as in a method illustrated in FIG. 1b. A microtiter plate was coated with an antigen PSA, and the culture supernatant containing phages was added thereto, followed by incubation for 1 hour. After washing three times, HRP (horse radish peroxidase)-conjugated anti-M13 antibody was added thereto. After incubation for 1 hour and washing three times, $H_2O_2$-added ABTS was added to examine color development. Then, absorbance at 405 nm was measured. As a control group, a wild-type phage was used. Even after 21 light chain residues and 27 heavy chain residues were replaced by cysteine, they showed affinity similar to that of the wild-type antibody (FIGS. 1c and 1d). In Tables 1a and 1b, sequential numbering and Kabat numbering of the Cys-modified antibodies, and a base sequence of the wild-type of each modified antibody are given.

TABLE 1a

Light chain framework

| Light chain | Cys mutant | Sequence numbering | Kabat numbering | Wild type amino acid |
|---|---|---|---|---|
| Framework 1 | LF1-2 | L3 | L5 | T |
|  | LF1-3 | L4 | L6 | Q |
|  | LF1-4 | L5 | L7 | P |
|  | LF1-11 | L12 | L14 | N |
|  | LF1-15 | L16 | L18 | T |
| Framework 2 | LF2-3 | L31 | L37 | Q |
|  | LF2-12 | L40 | L45 | V |
| Framework 3 | LF3-1 | L52 | L57 | N |
|  | LF3-2 | L53 | L58 | I |
|  | LF3-5 | L56 | L61 | R |
|  | LF3-7 | L58 | L63 | S |
|  | LF3-8 | L59 | L64 | G |
|  | LF3-9 | L60 | L65 | S |
|  | LF3-10 | L61 | L66 | T |
|  | LF3-13 | L64 | L69 | S |
|  | LF3-14 | L65 | L70 | T |
|  | LF3-20 | L71 | L76 | T |
|  | LF3-27 | L78 | L83 | A |
|  | LF3-31 | L82 | L87 | Y |
| Framework 4 | LF4-5 | L98 | L102 | T |
|  | LF4-9 | L102 | L106 | V |

TABLE 1b

Heavy chain framework

| Heavy chain | Cys mutant | Sequence numbering | Kabat numbering | Wild type amino acid |
|---|---|---|---|---|
| Framework 1 | HF1-1 | H1 | H1 | A |
|  | HF1-3 | H3 | H3 | T |
|  | HF1-5 | H5 | H5 | D |
|  | HF1-6 | H6 | H6 | E |
|  | HF1-7 | H7 | H7 | S |
|  | HF1-11 | H11 | H11 | L |
|  | HF1-12 | H12 | H12 | Q |
|  | HF1-13 | H13 | H13 | T |
|  | HF1-16 | H16 | H16 | G |
|  | HF1-18 | H18 | H18 | L |
|  | HF1-19 | H19 | H19 | S |

TABLE 1b-continued

Heavy chain framework

| Heavy chain | Cys mutant | Sequence numbering | Kabat numbering | Wild type amino acid |
|---|---|---|---|---|
| | HF1-24 | H24 | H24 | A |
| | HF1-25 | H25 | H25 | S |
| Framework 2 | HF2-7 | H42 | H42 | G |
| | HF2-13 | H48 | H48 | V |
| Framework 3 | HF3-4 | H70 | H69 | I |
| | HF3-7 | H73 | H72 | D |
| | HF3-9 | H75 | H74 | G |
| | HF3-10 | H76 | H75 | Q |
| | HF3-12 | H78 | H77 | T |
| | HF3-21 | H87 | H83 | R |
| | HF3-22 | H88 | H84 | A |
| | HF3-23 | H89 | H85 | E |
| | HF3-25 | H91 | H87 | T |
| | HF3-27 | H93 | H89 | T |
| Framework 4 | HF4-8 | H123 | H110 | I |
| | HF4-11 | H126 | H113 | S |

Figure 1E:
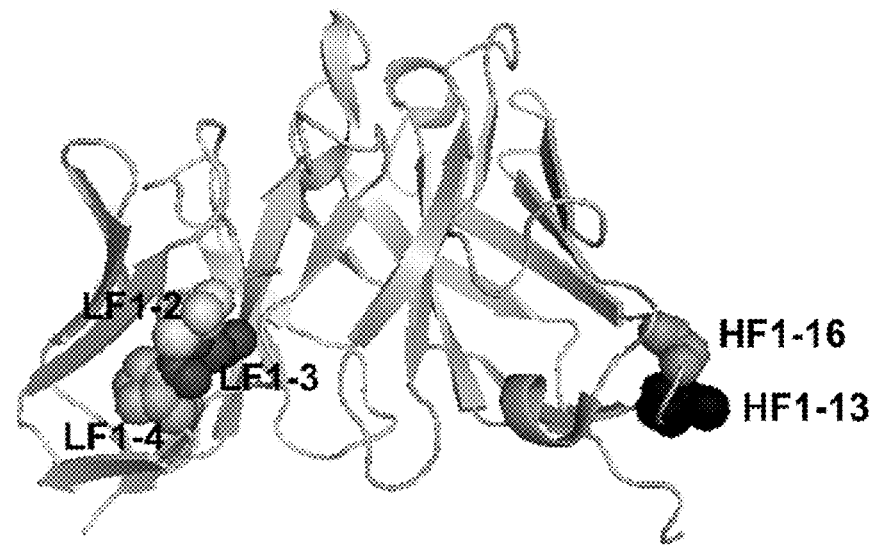
FIG. 1e shows a three-dimensional representation of a chicken antibody fragment derived by X-ray crystal coordinates, in which the structure positions of 5 types of the engineered Cys residues of the heavy and light chains are shown.

In order to examine solvent accessibility of the selected Cys-modified antibodies, solvent accessible surface area was examined by a three-dimensional structure of a chicken antibody fragment derived by X-ray crystal coordinates (literature [Shih H. H. et al., J Biol. Chem. (2012) 287: 44425-44434; PDB ID: 4GLR]), as shown in Tables 2a and 2b. Of them, structural positions of 5 types of base (LF1-2, LF1-3, LF1-4, HF1-13, HF1-16) residues are shown in FIG. 1e.

TABLE 2a

Solvent accessibility of light chain

| Light chain | Cys mutant | Solvent accessibility area ($A^2$) |
|---|---|---|
| Framework 1 | LF1-2 | 95.52 |
| | LF1-3 | 17 |
| | LF1-4 | 55.89 |
| | LF1-11 | 116.46 |
| | LF1-15 | 7.5 |
| Framework 2 | LF2-3 | 17.89 |
| | LF2-12 | 69.64 |
| Framework 3 | LF3-1 | 139.13 |
| | LF3-2 | 26.94 |
| | LF3-5 | 42.19 |
| | LF3-7 | 46.25 |
| | LF3-8 | 12.95 |
| | LF3-9 | 62.79 |
| | LF3-10 | 45.55 |
| | LF3-13 | 48.57 |
| | LF3-14 | 49.06 |
| | LF3-20 | 72.89 |
| | LF3-27 | 59.26 |
| | LF3-31 | 10.64 |
| Framework 4 | LF4-5 | 0 |
| | LF4-9 | 6.5 |

TABLE 2b

Solvent accessibility of heavy chain

| Heavy chain | Cys mutant | Solvent accessibility area ($A^2$) |
|---|---|---|
| Framework 1 | HF1-1 | 127.31 |
| | HF1-3 | 73.16 |
| | HF1-5 | 71.13 |
| | HF1-6 | 6.42 |
| | HF1-7 | 62.7 |
| | HF1-11 | 147.06 |
| | HF1-12 | 29.81 |
| | HF1-13 | 91.96 |
| | HF1-16 | 21.38 |
| | HF1-18 | 12.61 |
| | HF1-19 | 42.57 |
| | HF1-24 | 0.88 |
| | HF1-25 | 45.66 |
| Framework 2 | HF2-7 | 80.67 |
| | HF2-13 | 1.53 |
| Framework 3 | HF3-4 | 4.97 |
| | HF3-7 | 67.97 |
| | HF3-9 | 72.49 |
| | HF3-10 | 121.23 |
| | HF3-12 | 28.12 |
| | HF3-21 | 110.03 |
| | HF3-22 | 70.68 |
| | HF3-23 | 118.19 |
| | HF3-25 | 28.23 |
| | HF3-27 | 5.82 |
| Framework 4 | HF4-8 | 89.14 |
| | HF4-11 | 101.82 |

Example 2: Preparation of Antibody Having Two Cys Modifications

Figure 2:
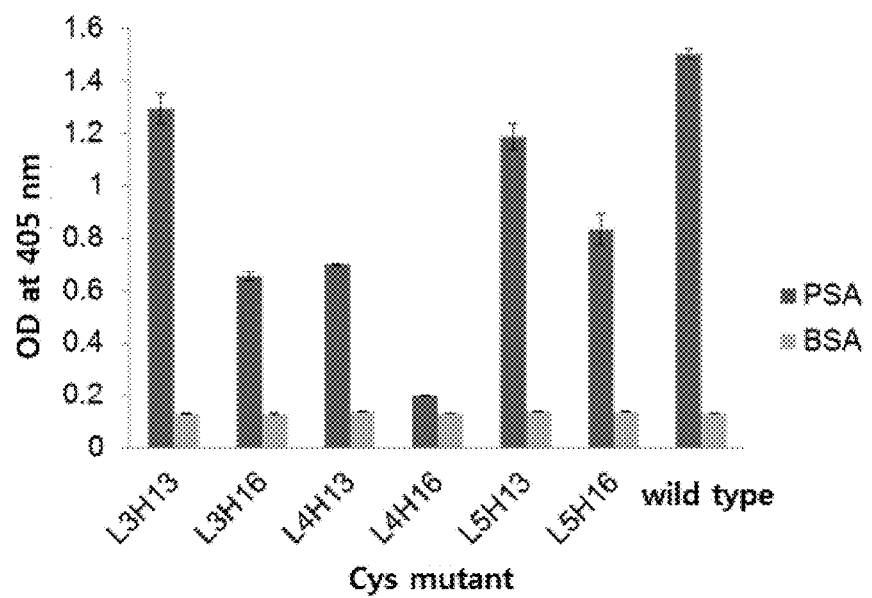
FIG. 2 shows binding measurements with detection of absorbance at 405 nm of antibody phages including two cysteine residues having thiol reactivity.

From the residues of light chain (L3, L4, L5) and heavy chain (H13, H16) according to sequential numbering, each one residue of the light chain and the heavy chain was replaced by cysteine in combination, and total 6 types (L3H13, L3H16, L4H13, L4H16, L5H13, L5H16) of Cys-modified antibody genes with two reactive cysteines were prepared by PCR. Next, they were expressed in the form of phage-displayed scFv as in Example 1, and then their affinity to PSA antigen was measured by enzyme-linked immunosorbent assay (FIG. 2).

Example 3: Modified Antibody Having Replacement of Amino Acid Residues Adjacent to Cys To replace amino acids flanking both sides of 5 types of Cys-modified antibodies (LF1-2, LF1-3, LF1-4, HF1-13 and HF1-16) prepared in Example 1-1 for efficient conjugation by cationic amino acids (arginine, lysine) or anionic amino acids (aspartic acid, glutamic acid), DNA base sequences (arginine; CGT, lysine; AAG, aspartic acid; GAT, glutamic acid; GAA) corresponding to the respective residues were inserted by PCR. scFv DNAs thus obtained were inserted into a phagemid vector pcomb3X, respectively and then transformed into E. coli ER2738. Next, the antibodies were incubated in the form of phage-displayed scFv in SB culture medium. Base sequences of the Cys-modified antibodies with replacement of cationic or anionic residues are given in Tables 3a and 3b.

Figure 3A:
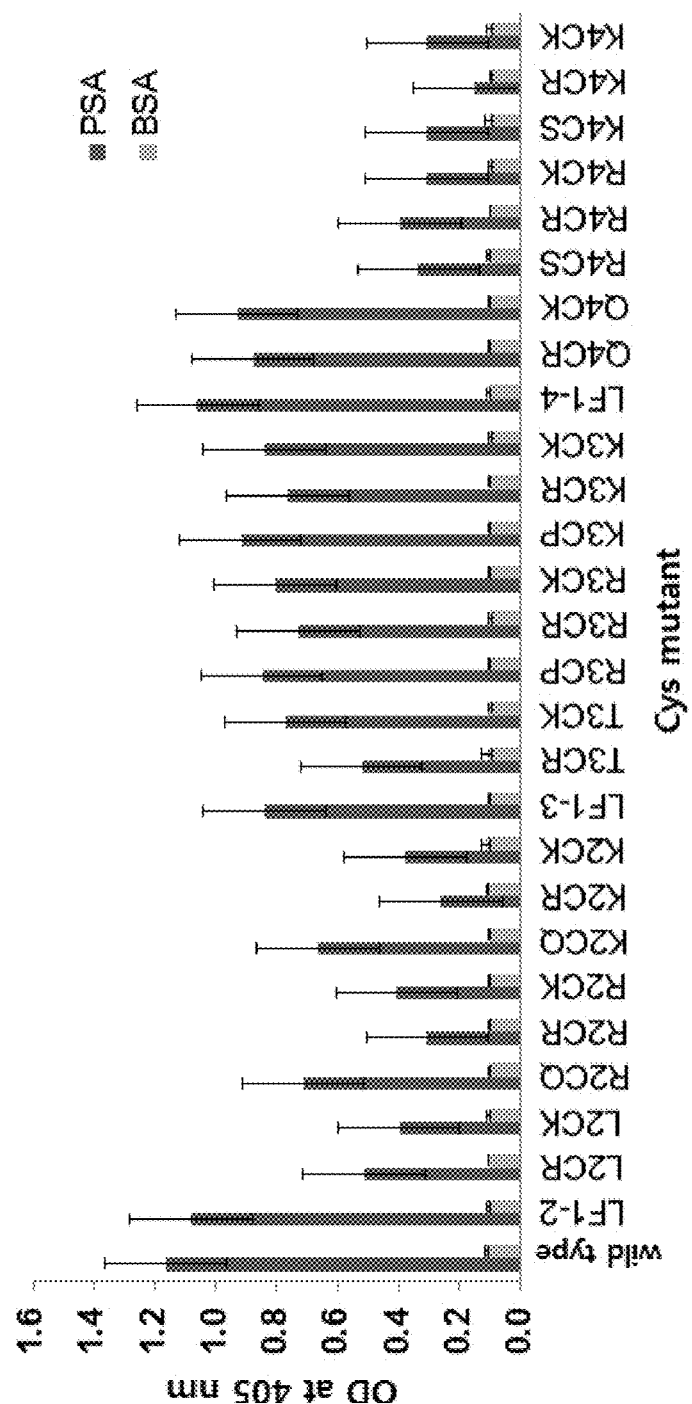
FIGS. 3a and 3b show binding measurements with detection of absorbance at 405 nm of Cys-modified antibody phages with replaced with cationic amino acids (upper: modified light chain, lower: modified heavy chain)
Figure 3B:
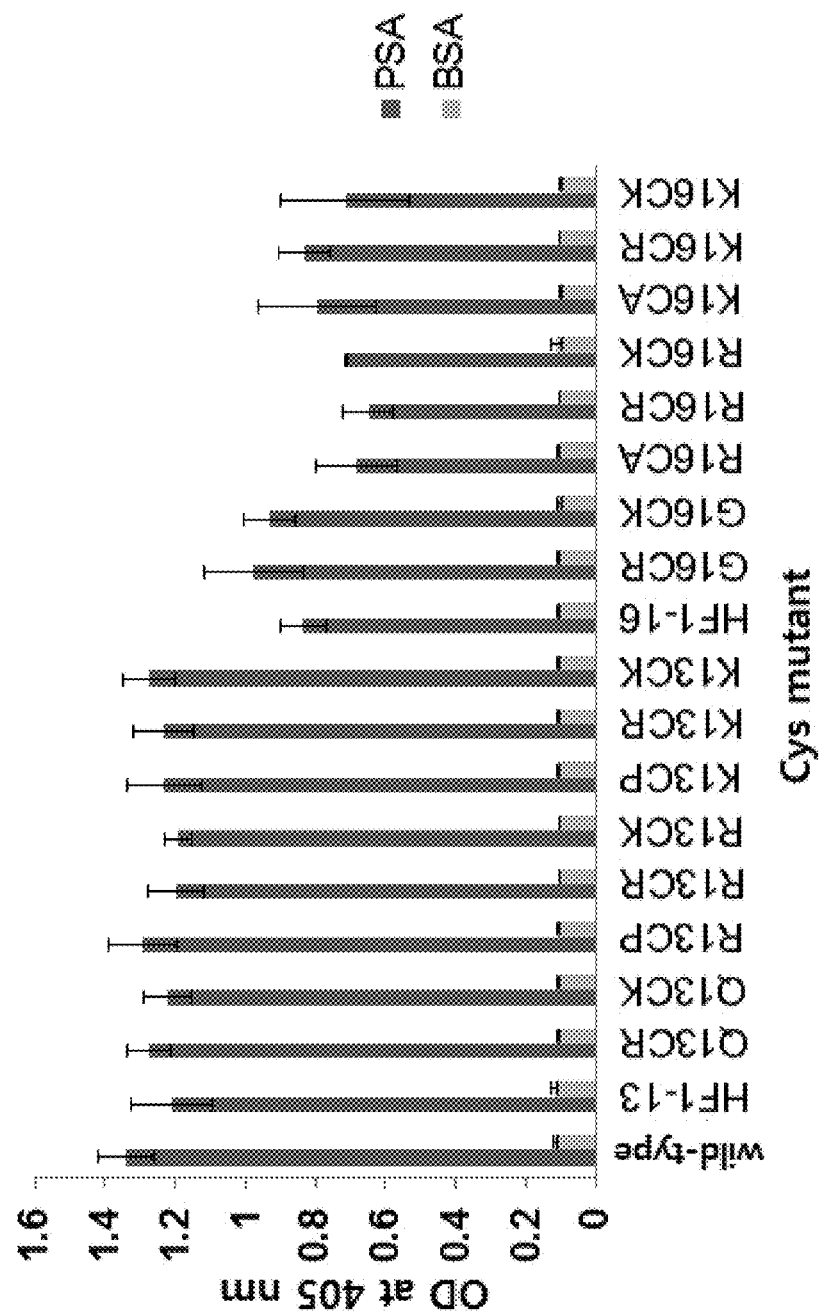
Figure 3C:
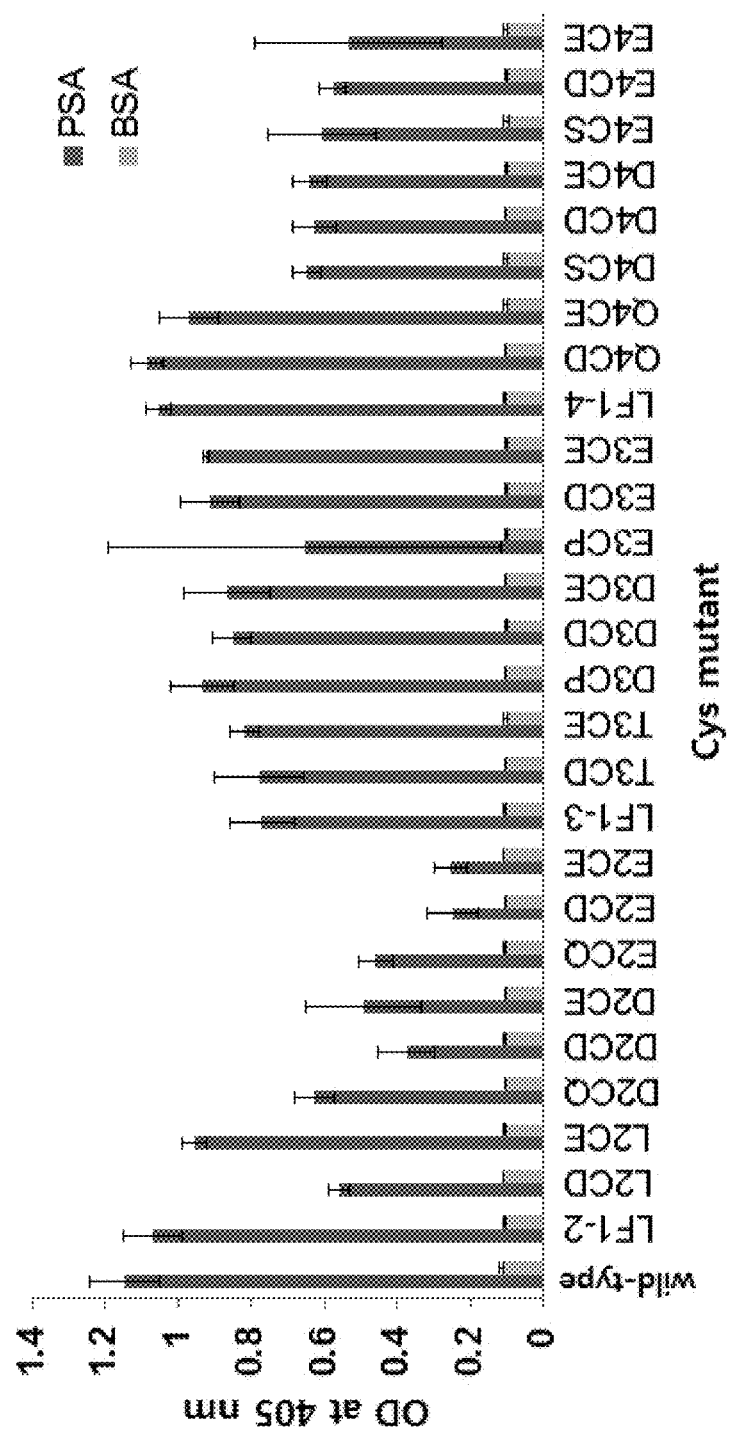
FIGS. 3c and 3d show binding measurements with detection of absorbance at 405 nm of Cys-modified antibody phages with replacement of anionic amino acid (upper: modified light chain, lower: modified heavy chain)
Figure 3D:
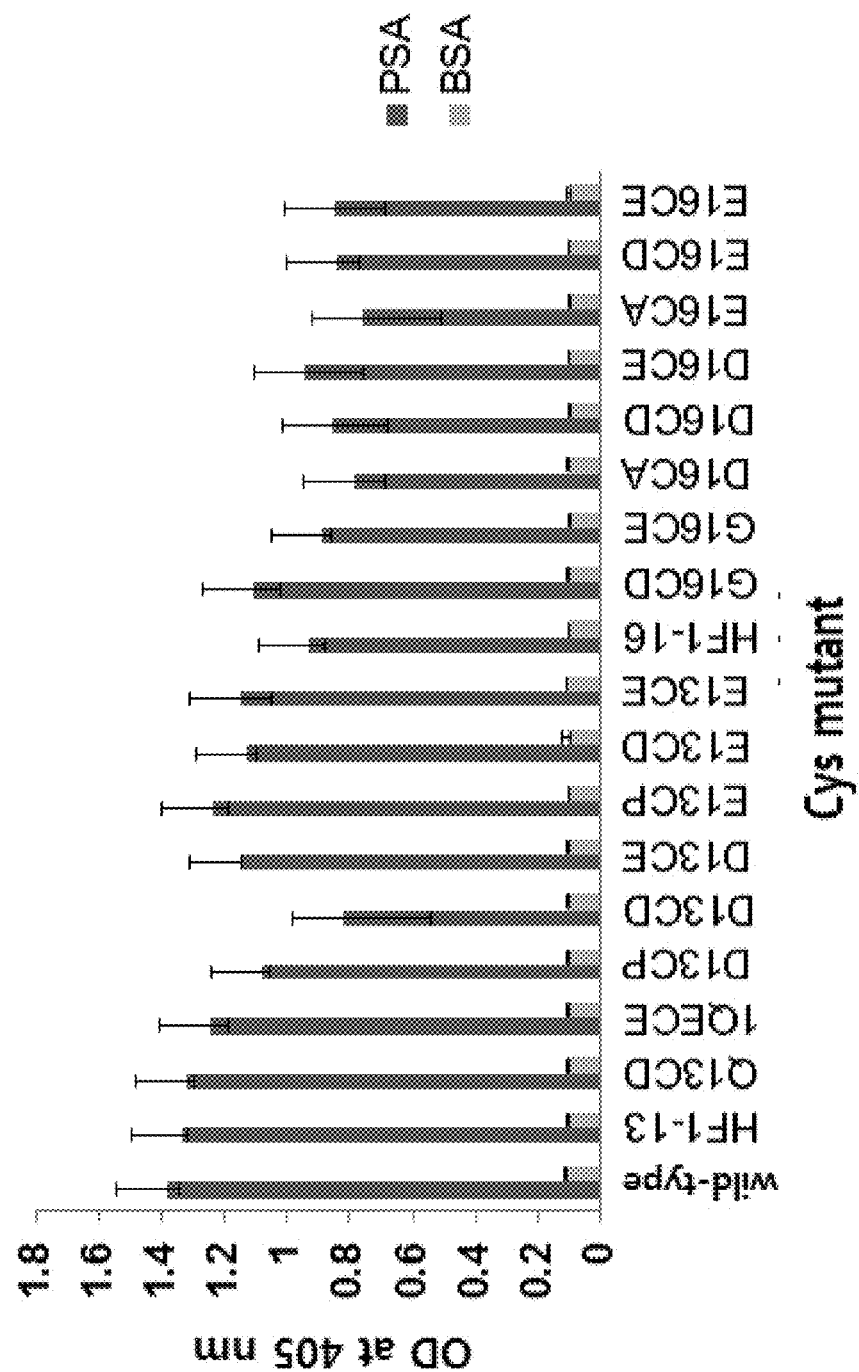

For measurement of antigen affinity, a microtiter plate was coated with an antigen PSA, and then the culture supernatant containing phages was added. After incubation for 1 hour and washing three times, HRP (horse radish peroxidase)-conjugated anti-M13 antibody was added thereto. After incubation for 1 hour and washing three times, $H_2O_2$-added ABTS was added to examine color development. Then, absorbance at 405 nm was measured. The result of cationic Cys-modified antibodies is shown in FIGS. 3a and 3b and the result of anionic Cys-modified antibodies are shown in FIGS. 3c and 3d.

| Mutant name | Sequence Kabat numbering (L3-L4-L5-L6-L7) | SEQ ID NO | Mutant name | Sequence Kabat numbering (L4-L5-L6-L7-L8) | SEQ ID NO | Mutant name | Sequence Kabat numbering (L5-L6-L7-L8-L9) | SEQ ID NO |
|---|---|---|---|---|---|---|---|---|
| L2CR | ALCRP | 9 | T3CR | LTCRS | 25 | Q4CR | TQCRS | 41 |
| L2CK | ALCKP | 10 | T3CK | LTCKS | 26 | Q4CK | TQCKS | 42 |
| R2CQ | ARCQP | 11 | R3CP | LRCPS | 27 | R4CS | TRCSS | 43 |
| R2CR | ARCRP | 12 | R3CR | LRCRS | 28 | R4CR | TRCRS | 44 |
| R2CK | ARCKP | 13 | R3CK | LRCKS | 29 | R4CK | TRCKS | 45 |
| K2CQ | AKCQP | 14 | K3CP | LKCPS | 30 | K4CS | TKCSS | 46 |
| K2CR | AKCRP | 15 | K3CR | LKCRS | 31 | K4CR | TKCRS | 47 |
| K2CK | AKCKP | 16 | K3CK | LKCKS | 32 | K4CK | TKCKS | 48 |
| L2CD | ALCDP | 17 | T3CD | LTCDS | 33 | Q4CD | TQCDS | 49 |
| L2CE | ALCEP | 18 | T3CE | LTCES | 34 | Q4CE | TQCES | 50 |
| D2CQ | ADCQP | 19 | D3CP | LDCPS | 35 | D4CS | TDCSS | 51 |
| D2CD | ADCDP | 20 | D3CD | LDCDS | 36 | D4CD | TDCDS | 52 |
| D2CE | ADCEP | 21 | D3CE | LDCES | 37 | D4CE | TDCES | 53 |
| E2CQ | AECQP | 22 | E3CP | LECPS | 38 | E4CS | TECSS | 54 |
| E2CD | AECDP | 23 | E3CD | LECDS | 39 | E4CD | TECDS | 55 |
| E2CE | AECEP | 24 | E3CE | LECES | 40 | E4CE | TECES | 56 |

| Mutant name | Sequence Kabat numbering (H11-H12-H13-H14-H15) | SEQ ID NO | Mutant name | Sequence Kabat numbering (H14-H15-H16-H17-H18) | SEQ ID NO |
|---|---|---|---|---|---|
| Q13CR | LQCRG | 57 | G16CR | PGCRL | 73 |
| Q13CK | LQCKG | 58 | G16CK | PGCKL | 74 |
| R13CP | LRCPG | 59 | R16CA | PRCAL | 75 |
| R13CR | LRCRG | 60 | R16CR | PRCRL | 76 |
| R13CK | LRCKG | 61 | R16CK | PRCKL | 77 |
| K13CP | LKCPG | 62 | K16CA | PKCAL | 78 |
| K13CR | LKCRG | 63 | K16CR | PKCRL | 79 |
| K13CK | LKCKG | 64 | K16CK | PKCKL | 80 |
| Q13CD | LQCDG | 65 | G16CD | PGCDL | 81 |
| Q13CE | LQCEG | 66 | G16CE | PGCEL | 82 |
| D13CP | LDCPG | 67 | D16CA | PDCAL | 83 |
| D13CD | LDCDG | 68 | D16CD | PDCDL | 84 |
| D13CE | LDCEG | 69 | D16CE | PDCEL | 85 |
| E13CP | LECPG | 70 | E16CA | PECAL | 86 |
| E13CD | LECDG | 71 | E16CD | PECDL | 87 |
| E13CE | LECEG | 72 | E16CE | PECEL | 88 |

Figure 4A:
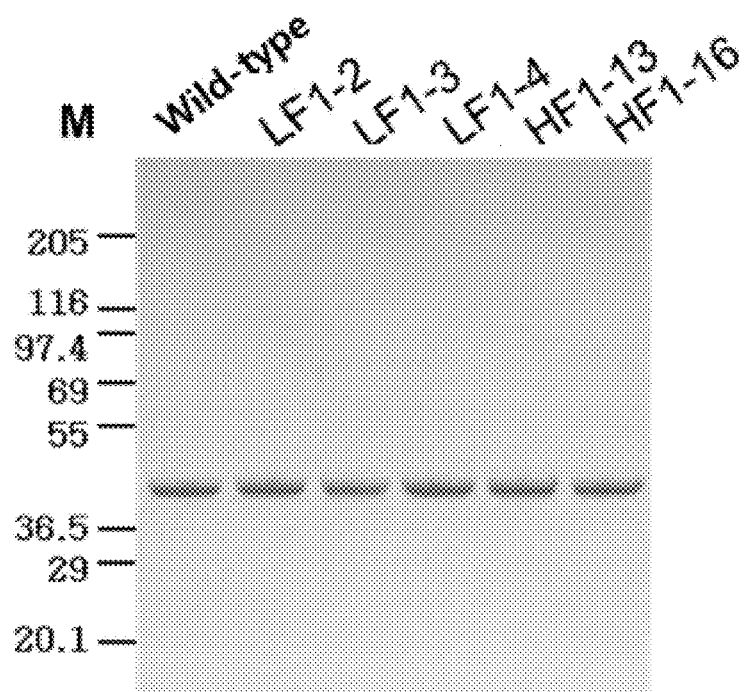
FIG. 4a shows coomassie blue staining of Cys-modified single chain Fv (scFv)-type antibodies expressed from cell culture for conjugation.

Example 4: Cys-Modified scFv Antibody 4-1. Expression and Purification of Cys-Modified scFv Antibody To prepare a fusion protein of Cys-modified scFv and human $C_{kappa}$, Cys-modified scFv was inserted into a mammalian expression vector pCEP4 containing human $C_{kappa}$ by cloning, and its expression was induced in HEK293F cells to obtain a final culture broth. Purification of the scFv-$C_{kappa}$ fusion protein from the culture broth was performed using kappa select beads. After purification, the protein was loaded on a polyacrylamide gel (SDS-PAGE gel), followed by electrophoresis. Expression and purification thereof were confirmed by Coomassie blue staining FIG. 4a shows the result of examining expression and purification of wild-type, LF1-2, LF1-3, LF1-4, HF1-13, and HF1-16 scFv proteins.

Figure 4B:
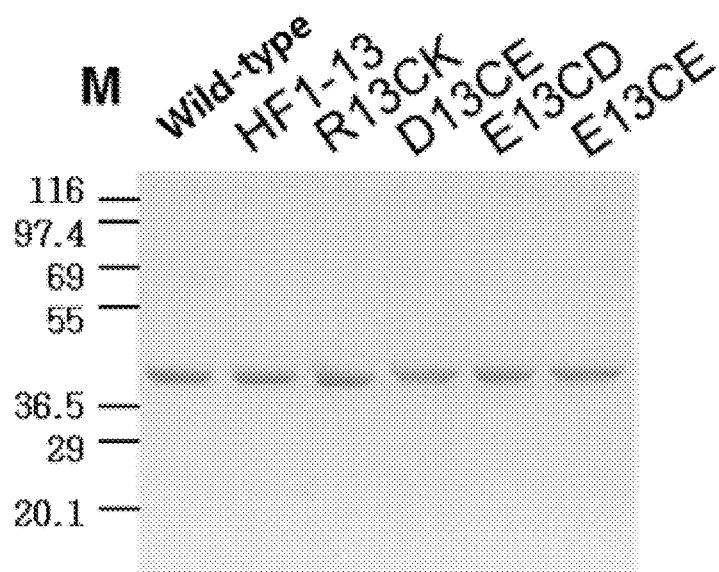
FIG. 4b shows coomassie blue staining of cationic or anionic Cys-modified scFv-type antibodies expressed from cell culture for conjugation.

4-2. Expression and Purification of Cys-Modified scFv Antibody Having Replacement of Amino Acid Residues Adjacent to Cys From the Cys-modified antibodies having replacement of amino acid residues adjacent to Cys with cationic or anionic amino acids, clones maintaining antigen affinity were selected and their fusion proteins with human $C_{kappa}$ were expressed in HEK293F cells as in Example 4-1, and purified using kappa select beads. Thereafter, electrophoresis was performed on a polyacrylamide gel, and their expression and purification were confirmed by coomassie blue staining FIG. 4b shows the result of examining expression and purification of wild-type, HF1-13, R13CK, D13CE, E13CD, and E13CE scFv-$C_{kappa}$ fusion proteins.

Figure 5A:
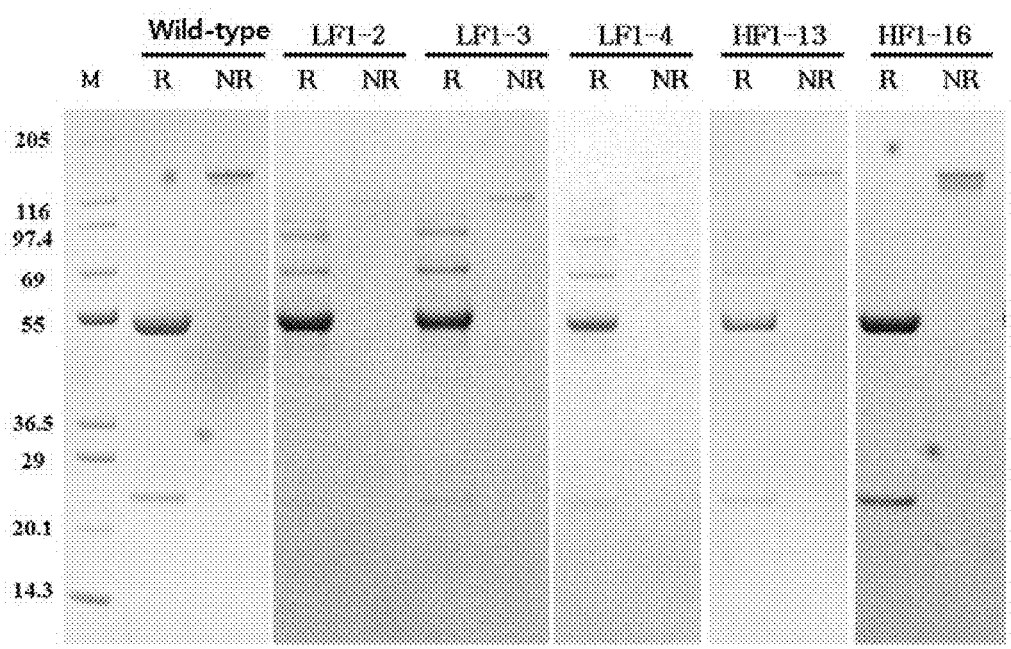
FIG. 5a shows coomassie blue staining of Cys-modified full IgG-type antibodies expressed from cell culture for conjugation.

Example 5: Cys-Modified Full IgG Antibody 5-1. Expression and Purification of Cys-Modified Full Antibody To prepare chicken-human chimeric full IgG protein, light chain and heavy chain DNAs of the variable region of Cys-modified antibody prepared in Example 1 were obtained by PCR and inserted into an IgG expression vector, followed by expression and culture in HEK293F cells. Thereafter, full IgG antibodies were purified using protein A beads. The purified proteins were electrophoresed, and their expression and purification were confirmed by coomassie blue staining. FIG. 5a shows the result of examining expression and purification of wild-type, LF1-2, LF1-3, LF1-4, HF1-13, and HF1-16 full IgG proteins.

5-2. Expression and Purification of Cys-Modified Full IgG Antibody Having Replacement of Amino Acid Residues Adjacent to Cys To express Cys-modified antibody having replacement of amino acid residues adjacent to Cys prepared in Example 3 in the form of chicken-human chimeric full IgG antibody as in Example 5-1, the antibody gene was inserted into an IgG expression vector, and expressed and cultured in HEK293F cells. Next, full IgG antibodies were purified from the culture broth using protein A beads. The purified proteins were loaded on a polyacrylamide gel, followed by electrophoresis. Expression and purification thereof were confirmed by coomassie blue staining. FIG. 5b shows the result of examining expression and purification of R13CK, E13CD, and E13CE full IgG proteins.

Figure 6:
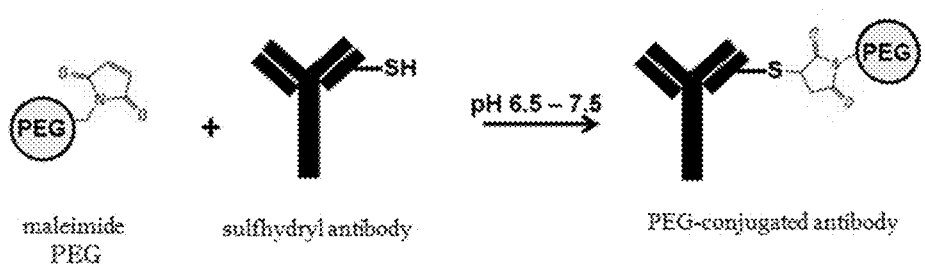
FIG. 6 shows a cartoon depiction of conjugation of maleimide activated PEG to Cys-modified antibody.

Example 6: PEG-Conjugated, Modified Antibody 6-1. Preparation of PEG-Cys-Modified Antibody by PEG Conjugation and Assay Thereof In accordance with a method described in the literature [Junutula et al., (2008) nature biotechnology 925-32], Cys-modified antibody prepared in Example 1 was reduced by addition of 10-fold TCEP, and then TCEP was removed. For partial oxidation, DHA was added in an amount corresponding to 2-fold of TCEP. Thereafter, maleimide PEG was added in an amount corresponding to 10-fold of the antibody, and incubated at 4° C. for 12 hours to induce conjugation of antibody with PEG. FIG. 6 shows a cartoon depiction of conjugation of maleimide PEG to sulfhydryl antibody.

Figure 7A:
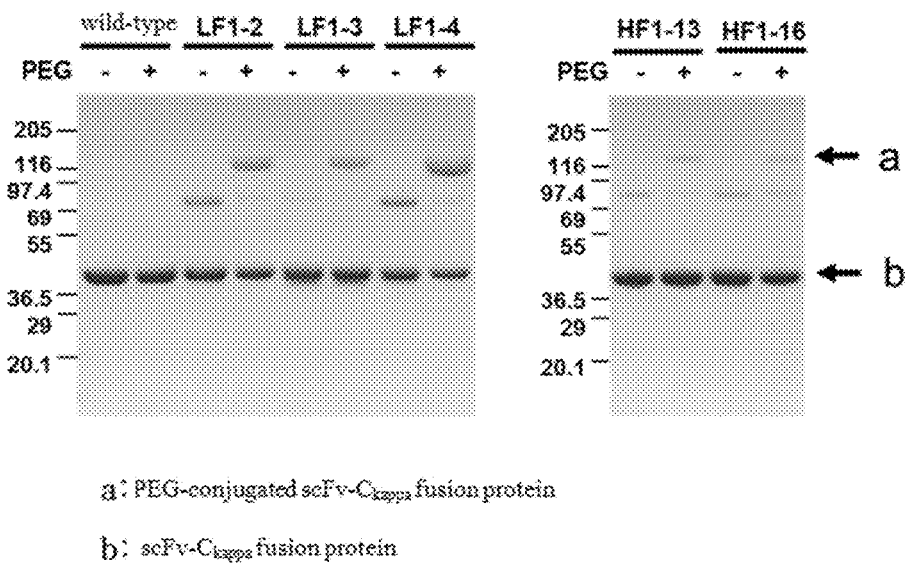
FIG. 7a shows coomassie blue staining of maleimide PEG-conjugated scFv.
Figure 8A:
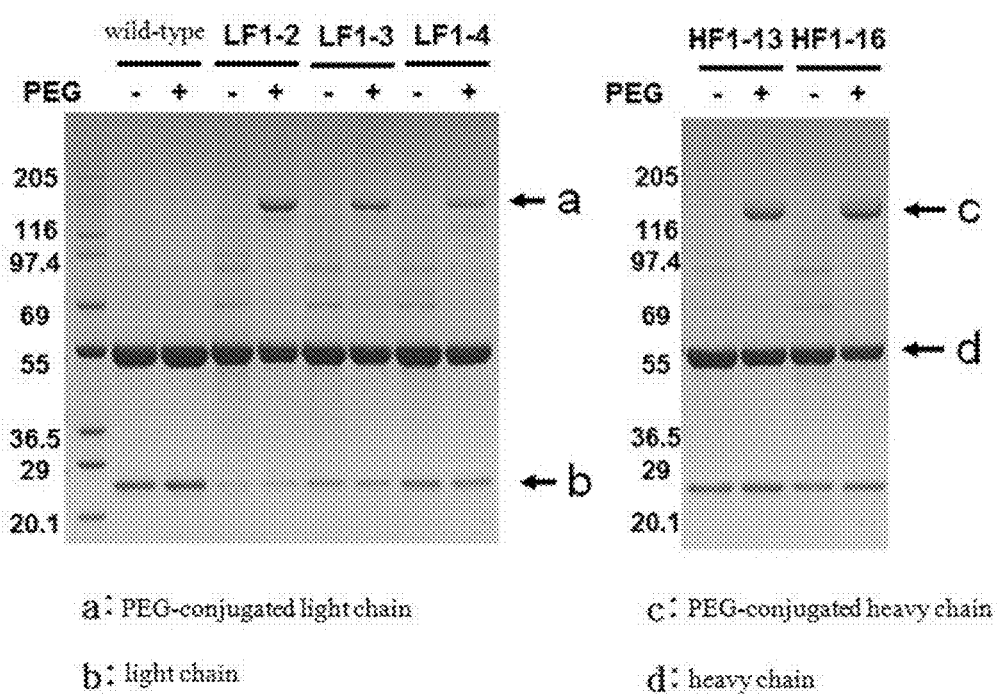
FIG. 8a shows coomassie blue staining of maleimide PEG-conjugated full IgG.

Antibody-PEG was loaded on a polyacrylamide gel, and then electrophoresed. Next, the gel was subjected to coomassie or iodine staining and immunoblotting to examine conjugation of PEG to antibody. For coomassie staining, the gel was stained with coomassie brilliant blue R250, and destained with a destaining solution containing methanol and acetic acid to identify the corresponding protein. FIG. 7a shows the result of wild-type, LF1-2, LF1-3, LF1-4, HF1-13, and HF1-16 scFv, and FIG. 8a shows the result of wild-type, LF1-2, LF1-3, LF1-4, HF1-13, and HF1-16 full IgG.

Figure 7B:
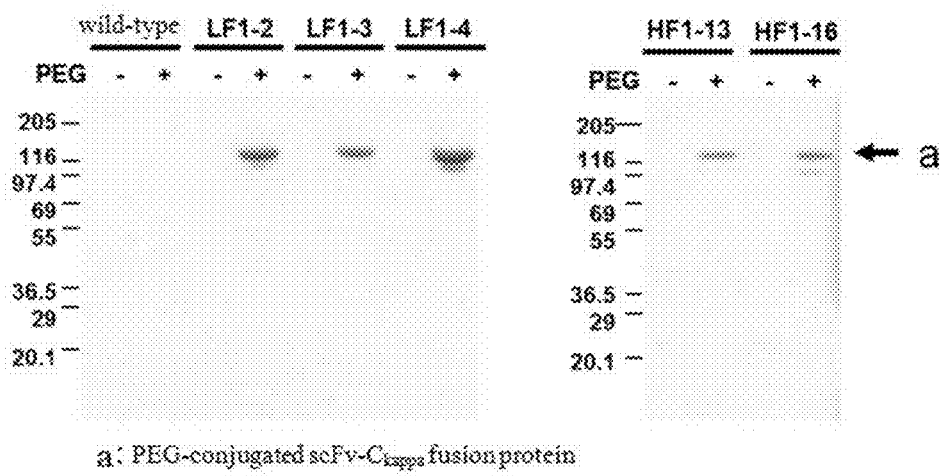
FIG. 7b shows iodine staining of maleimide PEG-conjugated scFv.
Figure 8B:
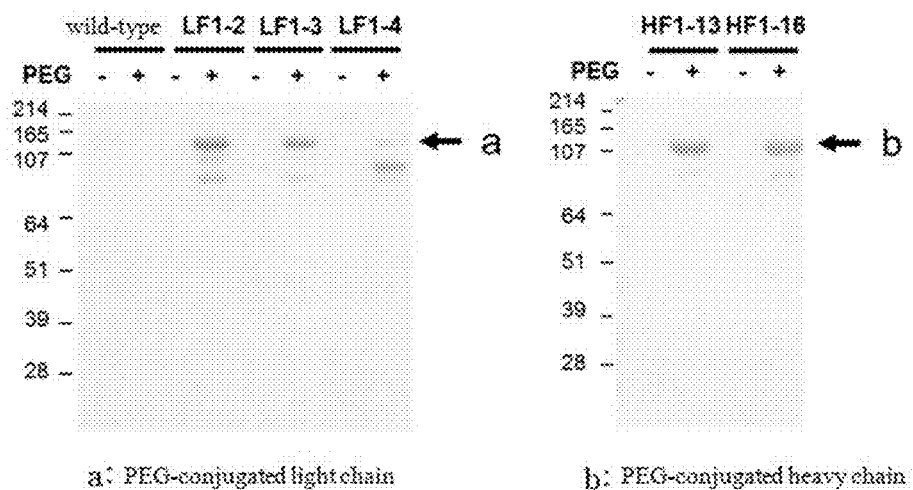
FIG. 8b shows iodine staining of maleimide PEG-conjugated full IgG.

For iodine staining, the polyacrylamide gel was washed with distilled water for 15 minutes, and then left in 5% $BlCl_2$ for 15 minutes. Next, the gel was stained with 0.1 M iodine for 10 minutes, and destained with distilled water for 10 minutes to detect only PEG. FIG. 7b shows the result of wild-type, LF1-2, LF1-3, LF1-4, HF1-13, and HF1-16 scFv, and FIG. 8b shows the result of wild-type, LF1-2, LF1-3, LF1-4, HF1-13, and HF1-16 full IgG.

Figure 7C:
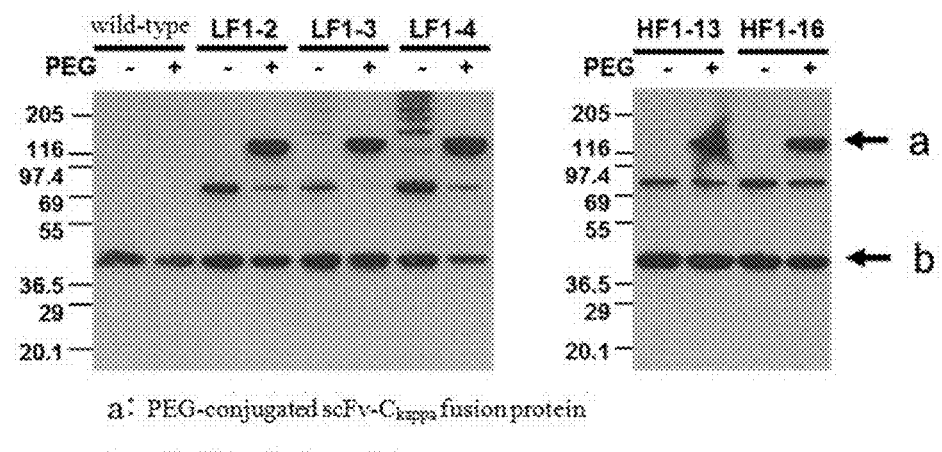
FIG. 7c shows immunoblotting of maleimide PEG-conjugated scFv.
Figure 8C:
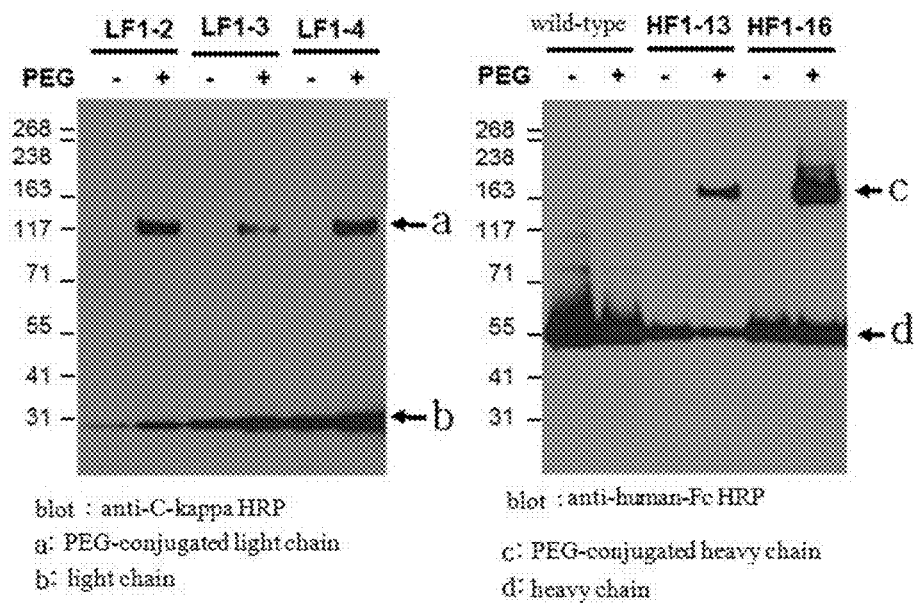
FIG. 8c shows immunoblotting of maleimide PEG-conjugated full IgG.

For immunoblotting, the polyacrylamide gel was separated according to the size of the protein, and then full IgG was transferred onto an NC membrane, and scFv-$C_{kappa}$ fusion protein and full IgG light chain region were detected using HRP-conjugated anti-$C_{kappa}$ antibody and full IgG heavy chain region was detected using HRP-conjugated anti-human Fc antibody. FIG. 7c shows the result of wild-type, LF1-2, LF1-3, LF1-4, HF1-13, and HF1-16 scFv, and FIG. 8c shows the result of wild-type, LF1-2, LF1-3, LF1-4, HF1-13, and HF1-16 full IgG.

6-2. Preparation of PEG-Cys-Modified Antibody Having Replacement of Amino Acid Residues Adjacent to Cys by PEG Conjugation and Assay Thereof The antibody having replacement of cationic or anionic residue was reduced using TCEP as in Example 6-1, and partially oxidized by addition of DHA. Next, PEG was added to the antibody to induce conjugation of PEG to the antibody. To examine antibody-PEG conjugation, coomassie blue staining, iodine staining and immunoblotting were performed.

Figure 9A:
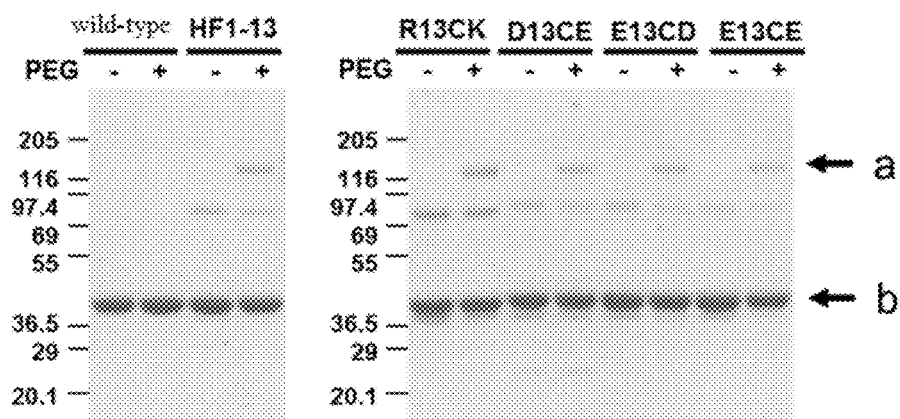
FIG. 9a shows coomassie blue staining of maleimide PEG-conjugated scFv with replacement of cationic or anionic residue.
Figure 10A:
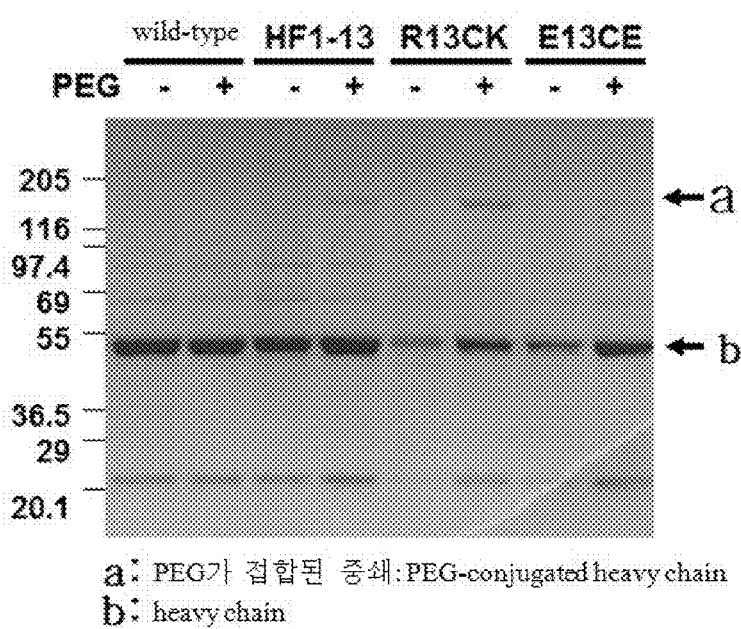
FIG. 10a shows coomassie blue staining of maleimide PEG-conjugated full IgG with replacement of cationic or anionic residue.

FIG. 9a shows the result of coomassie blue staining to examine conjugation of PEG to wild-type, HF1-13, R13CK, D13CE, E13CD, or E13CE scFv, and FIG. 10a shows the result of coomassie blue staining to examine conjugation of PEG to wild-type, HF1-13, R13CK, or E13CE full IgG.

Figure 9B:
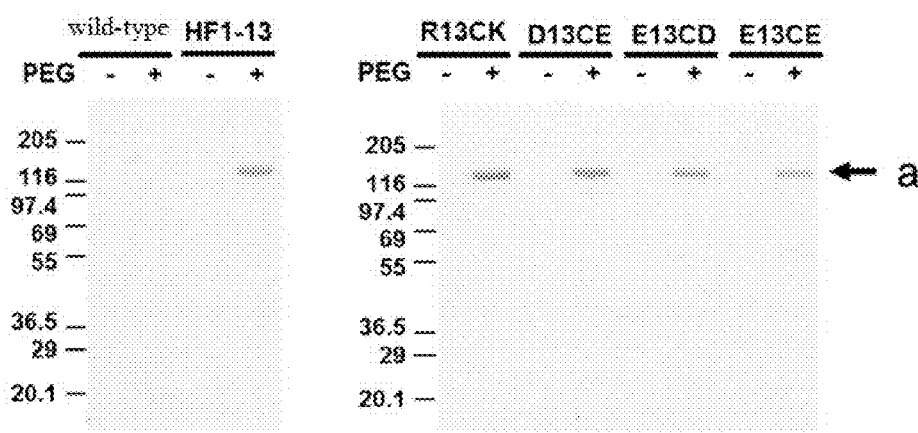
FIG. 9b shows iodine staining of maleimide PEG-conjugated scFv with replacement of cationic or anionic residue.
Figure 10B:
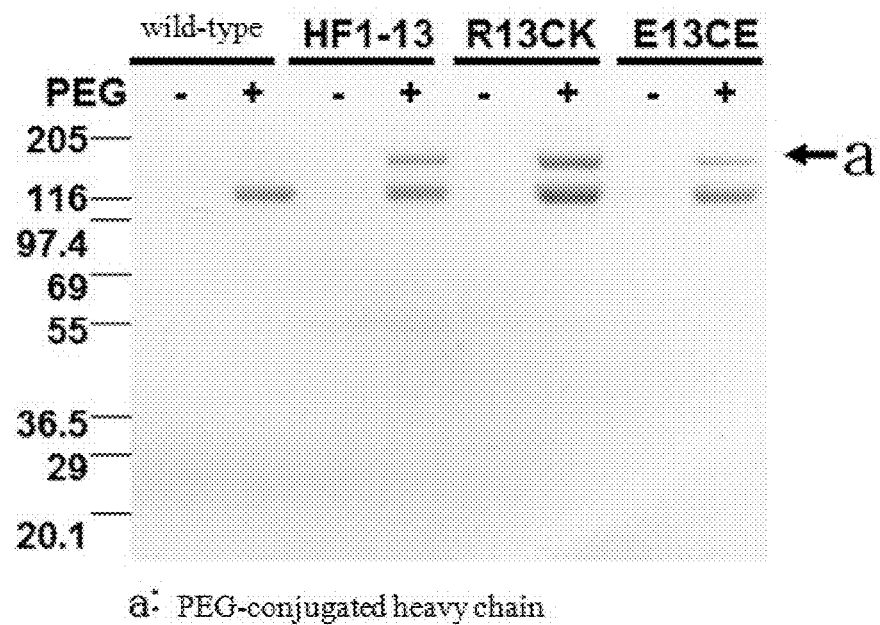
FIG. 10b shows iodine staining of maleimide PEG-conjugated full IgG with replacement of cationic or anionic residue.

FIG. 9b shows the result of iodine staining to examine conjugation of PEG to wild-type, HF1-13, R13CK, D13CE, E13CD, or E13CE scFv, and FIG. 10b shows the result of iodine staining of conjugation of PEG to HF1-13, R13CK, or E13CE full IgG.

Figure 9C:
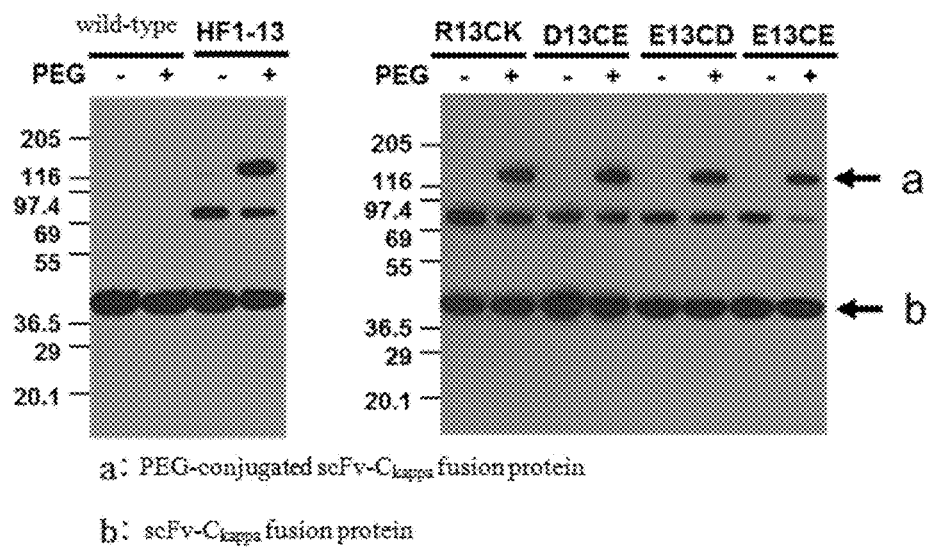
FIG. 9c shows immunoblotting of maleimide PEG-conjugated scFv with replacement of cationic or anionic residue.
Figure 10C:
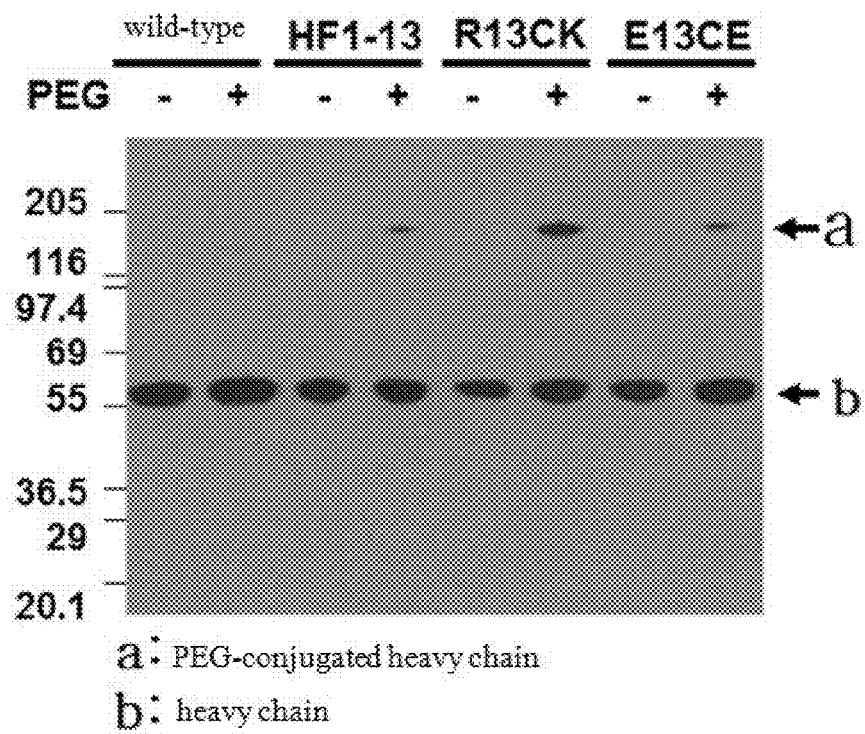
FIG. 10c shows immunoblotting of maleimide PEG-conjugated full IgG with replacement of cationic or anionic residue.

FIG. 9c shows the result of immunoblotting to examine conjugation of PEG to wild-type, HF1-13, R13CK, D13CE, E13CD, or E13CE scFv, and FIG. 10c shows the result of immunoblotting of conjugation of PEG to HF1-13, R13CK, or E13CE full IgG.

Figure 11A:
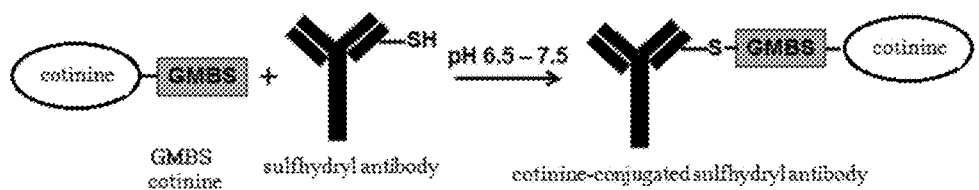
FIG. 11a shows a cartoon depiction of conjugation of GMBS-cotinine to Cys-modified antibody.

Example 7: Preparation of Antibody-Cotinine by Cotinine Conjugation and Assay Thereof Cys-modified antibody prepared in Example 1 was reduced by addition of 10-fold TCEP, and then TCEP was removed. For partial oxidation, DHA was added in an amount corresponding to 2-fold of TCEP. Thereafter, GMBS-cotinine was added in an amount corresponding to 10-fold of the antibody, and incubated at 4° C. for 12 hours to induce conjugation of antibody with cotinine. FIG. 11a shows a cartoon depiction of conjugation of GMBS-cotinine to sulfhydryl antibody.

Figure 11B:
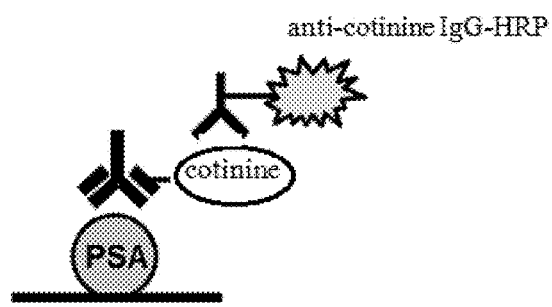
FIG. 11b shows a cartoon depiction of GMBS-cotinine-conjugated, Cys-modified antibody binding to immobilized PSA with binding of anti-cotinine HRP antibody for absorbance detection.
Figure 12:
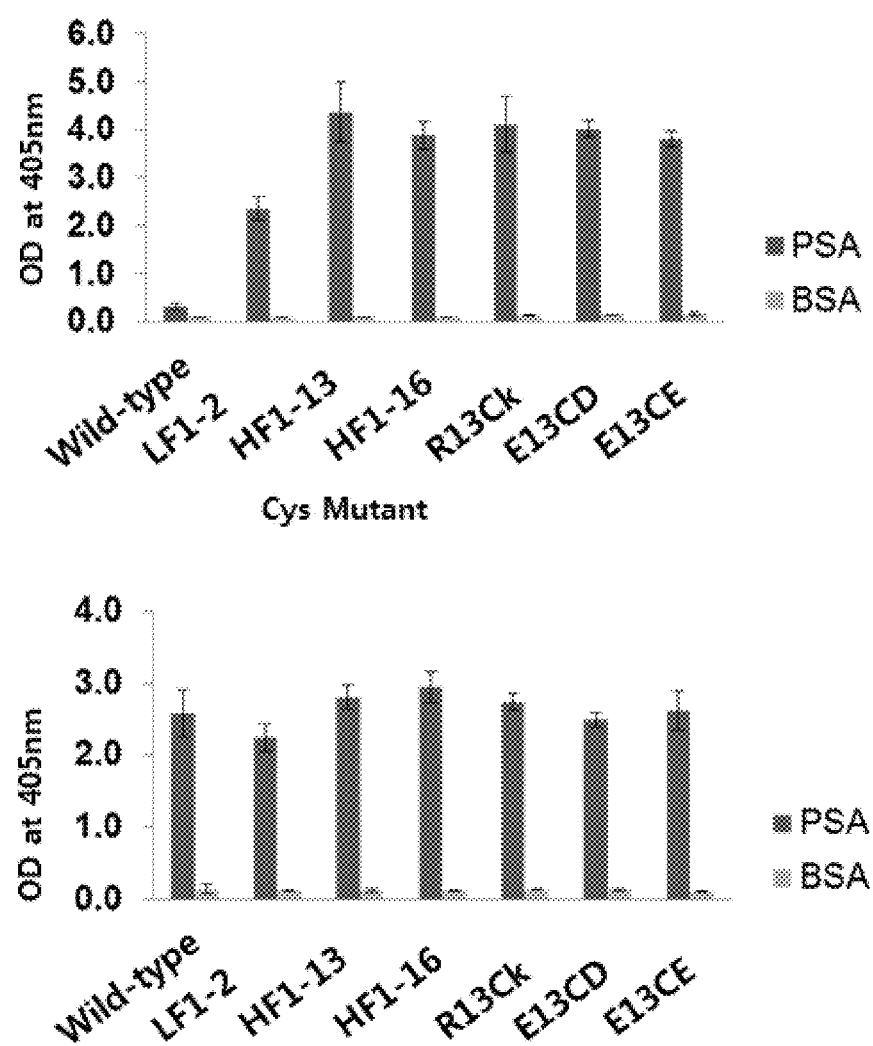
FIG. 12 shows detection of absorbance at 450 nm of binding of GMBS-cotinine to $C_{kappa}$-fused, Cys-modified scFv (upper: detection with anti-cotinine IgG-HRP, lower: detection with anti-$C_{kappa}$ IgG-HRP)
Figure 13A:
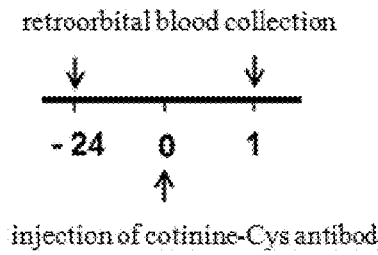
FIG. 13a shows injection time of cotinine-Cys into mice and blood collection time.
Figure 13B:
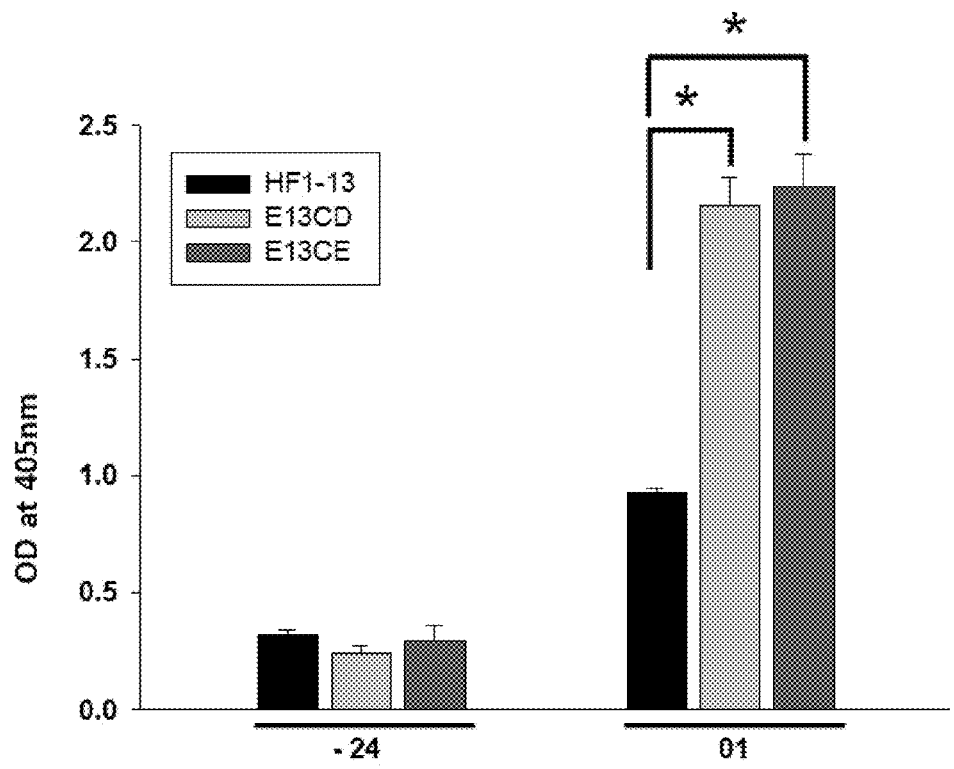
FIG. 13b shows detection of absorbance at 450 nm to examine the presence or absence of cotinine-Cys-modified antibody in the serum before and after injection of cotinine-Cys-modified antibody into mice.

Antibody-cotinine was assayed by enzyme-linked immunosorbent assay (ELISA) (FIG. 11b). A plate was coated with PSA antigen, and then antibody-cotinine was added thereto, followed by incubation for 1 hour. After washing three times, HRP-conjugated anti-cotinine IgG or anti-$C_{kappa}$ IgG antibody was added. After incubation for 1 hour and washing three times, TMB (3,3',5,5'-Tetramethylbenzidine) was added to examine color development, and then 2M $H_2SO_4$ was used to terminate the reaction. Absorbance at 450 nm was measured. In the result of FIG. 12, cotinine conjugation was confirmed by anti-cotinine IgG, and anti-$C_{kappa}$ IgG was used to detect only antibody, irrespective of cotinine conjugation.

Example 8: Injection of Antibody-Cotinine into Mouse and Assay of Cotinine-Antibody 6-week-old Balb/c mice were randomly divided into three groups (HF1-13, E13CD, E13CE), and then retroorbital blood collection was performed. After 24 hours, each 100 μg of 3 types of cotinine-scFv antibody $C_{kappa}$ fusion proteins prepared in Example 7 was intravenously injected into mice. 1 hour after cotinine-antibody injection, retroorbital blood collection was performed, and sera were separated using a centrifuge. The separated sera were diluted 50-fold in order to examine the presence or absence of cotinine-antibody in the sera, and enzyme-linked immunosorbent assay was performed as in Example 9. All procedures using mice were performed after inhalation anesthesia in order to minimize pain.

The invention claimed is:

1. An isolated cysteine-modified chicken antibody that binds to prostate specific antigen comprising at least one modified light chain framework or at least one heavy chain framework, wherein the at least one modified light chain framework comprises an amino acid sequence selected from the group consisting of SEQ ID NO:9 to SEQ ID NO: 56 and the at least one modified heavy chain framework comprises the amino acid sequence selected from the group consisting of SEQ ID NO: 57 to SEQ ID NO: 88.

2. The modified chicken antibody of claim 1, wherein the modified antibody is prepared by a method comprising
   introducing a mutation a nucleic acid sequence encoding the modified antibody;
   expressing the modified antibody; and
   isolating and purifying the modified antibody.

3. An antibody complex prepared by conjugating the modified chicken antibody of claim 1 with one or more compounds selected from the group consisting of a drug, an enzyme, an aptamer, a toxin, an affinity ligand, and a detection label.

* * * * *